(12) United States Patent
Malone et al.

(10) Patent No.: US 9,365,575 B2
(45) Date of Patent: Jun. 14, 2016

(54) KINASE INHIBITORS

(71) Applicant: Allergan, Inc., Irvine, CA (US)

(72) Inventors: Thomas C. Malone, Irvine, CA (US);
Julie A. Wurster, Irvine, CA (US);
Clarence Eugene Hull, III, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 35 days.

(21) Appl. No.: 13/897,837

(22) Filed: May 20, 2013

(65) Prior Publication Data

US 2013/0310394 A1 Nov. 21, 2013

Related U.S. Application Data

(60) Provisional application No. 61/649,516, filed on May 21, 2012.

(51) Int. Cl.
*C07D 487/04* (2006.01)
*C07D 455/00* (2006.01)

(52) U.S. Cl.
CPC .................................. *C07D 487/04* (2013.01)

(58) Field of Classification Search
CPC ........................... C07D 487/04; C07D 455/00
USPC ......................................... 514/267; 544/250
See application file for complete search history.

(56) References Cited

U.S. PATENT DOCUMENTS

| | | | |
|---|---|---|---|
| 4,585,772 A | 4/1986 | Junge et al. | |
| 5,990,109 A | 11/1999 | Chen et al. | |

OTHER PUBLICATIONS

Jo et al., Inhibition of Platelet-Derived Growth Factor B Signaling Enhances the Efficacy of Anti-Vascular Endothelial Growth Factor Therapy in Multiple Models of Ocular Neovascularization, American Journal of Pathology, vol. 168, No. 6, Jun. 2006, pp. 2036-2053.
Arora et al., Role of Tyrosine Kinase Inhibitors in Cancer Therapy, The Journal of Pharmacology and Experimental Therapeutics, vol. 315, No. 3, Jun. 29, 2005, pp. 971-979.
Barakat et al., VEGF Inhibitors for the Treatment of Neovascular Age-Related Macular Degeneration, Expert Opinion, 2009, pp. 637-646.
Bergers et al., Benefits of Targeting Both Pericytes and Endothelial Cells in the Tumorvasculature With Kinase Inhibitors, J. Clin. Invenst., 111, 2003, pp. 1287-1295.
Chappelow et al., Neovascular Age-Related Macular Degeneration Potential Therapies, Cole Eye Institute, 2008, pp. 1029-1036.
Cowan-Jacob, S.W., Structural Biology of Protein Tyrosine Kinases, Cellular and Molecular Life Sciences, 2006, pp. 2608-2625.
Stommel et al., Coactivation of Receptor Tyrosine Kinases Affects the Response of Tumor Cells to Targeted Therapies, Science, vol. 318, Oct. 12, 2007, pp. 287-290.
Heidenreich et al., Angiogenesis: The New Potential Target for the Therapy of Psoriasis? Drugs News Perspect, 21 (2), Mar. 2008, pp. 97-105.
Ni et al., Emerging Pharmacologic Therapies for Wet Age-Related Macular Degeneration, Ophthalmologica, 2009, pp. 401-410.
Smith et al., Expression of Vascular Endothelial Growth Factor and its Receptors in Rosacea, Br. J. Ophthalmol, 2007, pp. 226-229.
Zhang et al., Vascular Endothelial Growth Factor-A: A Multifunctional Molecular Player in Diabetic Retinopathy, The International Journal of Biochemistry & Cell Biology, 2009, pp. 2368-2371.
Lombardia et al., Synthesis of Optically Active Heterocyclic Compounds by Preparation of 1,3-Dinitro Derivatives and Enzymatic Enantioselective Desymmetrization of Prochiral Diamines; Eur. J. Org. Chem., 2010, pp. 484-493.
Cieslak, Jacek et al., Assessment of 4-Nitrogenated Benzyloxymethyl Groups for 2-Hydroxyl Protection in Solid-Phase RNA Synthesis, Organic Letters 2007, 9: 671-674, 4.
Iwasawa, Tetsuo et al., A Reversible Reaction Inside a Self-Assembled Capsule, JACS 2006, 128: 9308-9309.
Notification of the Transmittal of the Intl Search Report & Written Opinion mailed on Jul. 4, 2013 for PCT Application PCT/US13/041846 filed on May 20, 2013 in the name of Allergan, Inc.

*Primary Examiner* — Kendra D Carter
(74) *Attorney, Agent, or Firm* — Jonathan Bass

(57) ABSTRACT

The present invention relates to compounds of Formula I

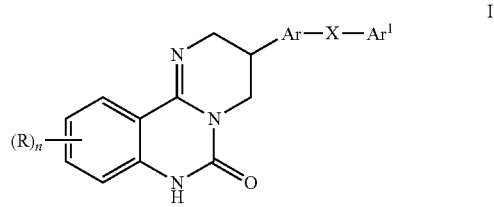

or a pharmaceutically acceptable salt thereof, wherein variables R, Ar, X, and Ar¹ and n are as defined herein. The compounds are capable of modulating tyrosine kinase signal transduction in order to regulate, modulate and/or inhibit abnormal cell proliferation.

11 Claims, No Drawings

KINASE INHIBITORS

CROSS REFERENCE TO RELATED APPLICATION

This application claims the benefit of U.S. Provisional Application Ser. No. 61/649,516 filed on May 21, 2012, all of which is incorporated herein by reference herein in its entirety.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life. Sci., 2996, 63, 2608-2625 which is incorporated herein by reference.

There are a number of examples where RTK kinases, have been found to be involved in cellular signaling pathways leading to pathological conditions, including exudative age-related macular degeneration (Ni et al. Ophthalmologica 2009 223 401-410; Chappelow et al. Drugs 2008 68 1029-1036), diabetic retinopathy (Zhang et al., Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105), rosacea (Smith, J. R., V. B. Lanier, et al. *Br J Ophthalmol* 2007, 91(2): 226-229) and hyper immune response. In ophthalmic diseases such as exudative age-related macular degeneration and diabetic retinopathy aberrant activation of VEGF receptors can lead to abnormal blood vessel growth. The importance of VEGFR signaling in the exudative age-related macular degeneration disease process is evident by the clinical success of multiple anti-VEGF targeting agents including Lucentis®, Avastin®, and EYLEA™ (Barakat et al., Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as exudative age-related macular degeneration and diabetic retinopathy the inhibition of both VEGFR and PDGFRβ☐ may provide a greater therapeutic effect in by causing regression of existing neovascular blood vessels present in the disease (Adamis et al., Am. J. Pathol. 2006 168 2036-2053). In cancer inhibition of multiple RTK signaling pathways has been suggested to have a greater effect than inhibiting a single RTK pathway (DePinho et al., Science 2007 318 287-290; Bergers et al. J. Clin Invest. 2003 111 1287-1295).

The identification of effective small compounds which specifically inhibit signal transduction by modulating the activity of receptor and non-receptor tyrosine kinases to regulate and modulate abnormal or inappropriate cell proliferation is therefore desirable and one object of this invention.

The above references are hereby incorporated by reference in their entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction by blocking the VEGF and/or PDGF receptors. Such compounds are useful for the treatment of diseases related to unregulated tyrosine kinase signal transduction, including vascular proliferative disorders such as diabetic retinopathy, age-related macular degeneration and retinopathy of prematurity.

In one illustrative embodiment, the compounds of the present invention have the following general formula I:

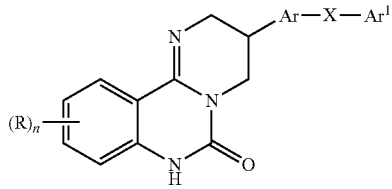

Wherein
Ar is an aryl group;
$Ar^1$ is an aryl group;
X is

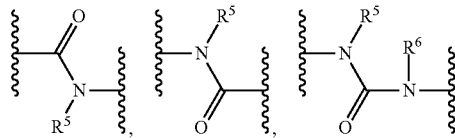

R is selected from the group consisting of halogen, lower alkyl, $OC(O)R^4$, $(CR^1R^2)_aC(O)OR^3$, $(CR^1R^2)_aOR^3$, $(CR^1R^2)_aN(R^4)C(O)R^3$, $(CR^1R^2)_aC(O)N(R^3)_2$, $(CR^1R^2)_aN(R^4)C(O)OR^3$, $(CR^1R^2)_aN(R^4)C(O)N(R^3)_2$, $(CR^1R^2)_aN(R^3)_2$, wherein $N(R^3)_2$ may form a heterocyclic ring optionally substituted with one or more of halogen and lower alkyl;

$R^1$, $R^2$ and $R^4$ are independently selected from the group consisting of hydrogen, halogen and lower alkyl;

$R^3$ is selected from the group consisting of hydrogen and lower alkyl;

$R^5$ is selected from hydrogen and lower alkyl;
$R^6$ is selected from hydrogen and lower alkyl;
a is 0 or an integer of from 1 to 4;
n is 0 or an integer of from 1 to 4 and prodrugs, pharmaceutically acceptable salts, racemic mixtures and enantiomers of said compound.

Preferably, a is 0.
Preferably, n is 0 or 1.
More preferably, n is 0.
Preferably, Ar is a carbocyclic aryl;
More preferably, Ar is phenyl.
Preferably, $Ar^1$ is selected from the group consisting of phenyl, furanyl and halo, lower alkyl, lower alkyloxy, lower alkylthio and halo-lower alkyl-substituted phenyl and furanyl.

More preferably, $Ar^1$ is selected from the group consisting of phenyl, furanyl and methyl, methoxy, methylthio, bromo, fluoro, trifluoro and chloro-substituted phenyl and furanyl.

Even more preferably, $Ar^1$ is selected from the group consisting of fluoro and trifluoro-substituted phenyl.

Preferably, R is hydrogen or acetate.
More preferably, R is hydrogen, i.e. n is 0.
Preferably, $R^5$ and $R^6$ are hydrogen and/or methyl; more preferably at least one of $R^5$ and $R^6$ is hydrogen.

Preferably, said compound has an $IC_{50}$ value for compound inhibition in the VEGFR2 Kinase Assay of less than 1000 nM.

More preferably, said compound has an $IC_{50}$ value for compound inhibition in the VEGFR2 Kinase Assay of less than 500 nM.

In another illustrative embodiment, the compound of the present invention is a 4-aryl-substituted-(2H)-pyrimido[1,2-c]quinazoline-6-oxo, or a pharmaceutically acceptable salt thereof, wherein said 4-aryl is substituted with a carboamino, or an aminocarbo or an aminocarboamino aryl group and wherein said compound binds to a tyrosine kinase receptor (such as a VEGF or a PDGF receptor).

In another embodiment, the 4-aryl-substituted-(2H)-pyrimido[1,2-c]quinazoline-6-oxo compound is phenyl-substituted-(2H)-pyrimido[1,2-c]quinazoline-6-oxo.

In another embodiment, the carboamino, aminocarbo or aminocarboamino aryl group a carboamino, aminocarbo or aminocarboamino phenyl group.

Compounds of formula I are useful as kinase inhibitors. As such, compounds of formula I will be useful for treating diseases related to unregulated tyrosine kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, pterygium, arthritis, restenosis, hepatic cirrhosis, atherosclerosis, psoriasis, rosacea, diabetes mellitus, wound healing, inflammation and neurodegenerative diseases and preferably ophthalmic diseases, i.e. diabetic retinopathy, age-related macular degeneration, retinopathy of prematurity, etc.

DETAILED DESCRIPTION OF THE INVENTION

The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy The following defined terms are used throughout this specification:

"Ac" refers to acetyl
"BOP" refers to Benzotriazole-1-yl-oxy-tris-(dimethylamino)-phosphonium hexafluorophosphate
"DMF" refers to dimethylformamide.
"Et" refers to ethyl.
"HBTU" refers to O-Benzotriazole-N,N,N',N'-tetramethyl-uronium-hexafluorophosphate
"iPr" refers to i-propyl.
"Me" refers to methyl.
"MeOH" refers to methanol
"PDGF" refers to platelet derived growth factor
"Ph" refers to phenyl
"PTKs" refers to protein tyrosine kinase
"RTKs" refers to receptor tyrosine kinase
"rt" refers to room temperature
"tBu" refers to t-butyl.

"THF" refers to tetrahydrofuran

"VEGF" refers to vascular endothelial growth factor

"VEGFR" refers to vascular endothelial growth factor receptor

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halo, nitrogen, oxygen, sulfur or phosphorus atom, e.g. fluoro, chloro, cyano, nitro, dialkylamino, hydroxyl, phosphate, thiol, etc.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts may also refer to those salts which retain the biological effectiveness and properties of the free acid and which are obtained by reaction with inorganic bases such as sodium hydroxide, calcium hydroxide, magnesium hydroxide, zinc hydroxide or by organic bases such as tromethamine, choline, diethylamine and lysine and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkoxy" refers to O-alkyl.

"Alkoxycarbonyl" refers to —C(O)O-alkyl or —C(O)O-aryl.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Carbocyclic aryl" refers to an aryl group wherein the ring atoms are carbon.

"Heteroaryl" or "heterocyclic aryl" refers to an aryl group having from 1 to 3 heteroatoms as ring atoms, the remainder of the ring atoms being carbon. Heteroatoms include oxygen, sulfur, and nitrogen. Thus, heteroaryl groups include furanyl, thienyl, pyridyl, pyrrolyl, N-lower alkyl pyrrolo, pyrimidyl, pyrazinyl, imidazolyl and the like.

The compounds of this invention may be prepared by the general reaction schemes set forth below.

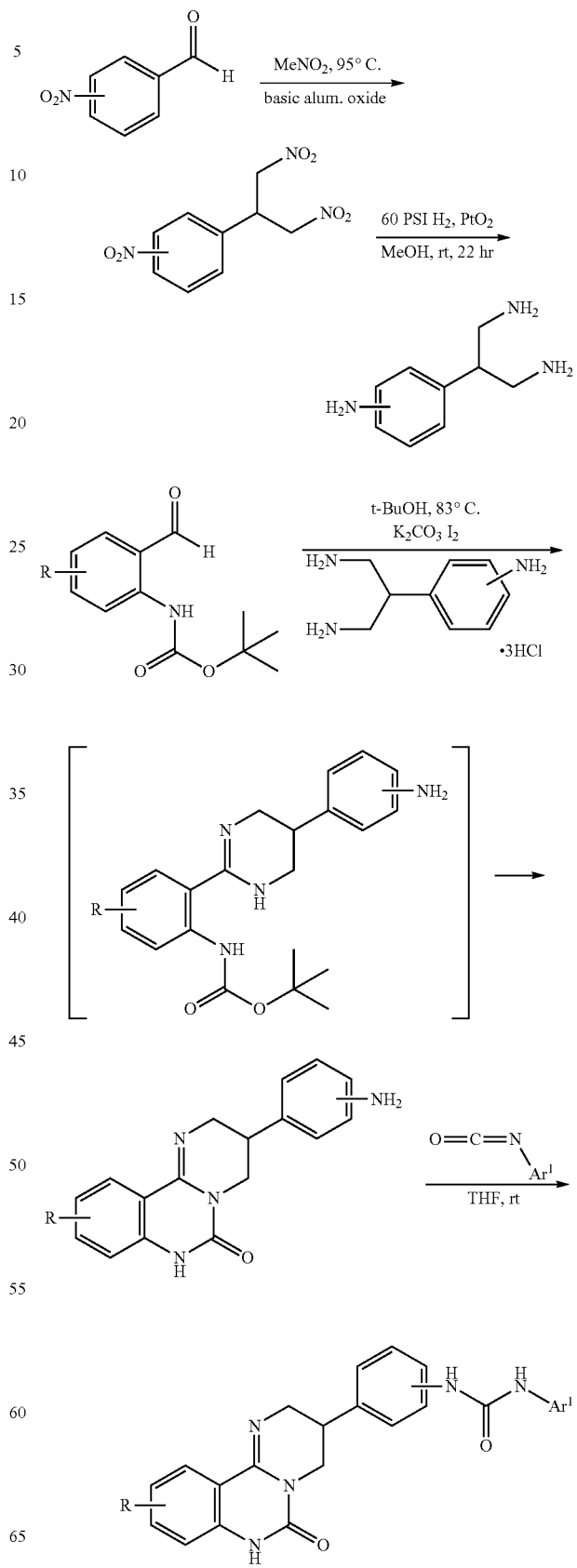

Scheme 1

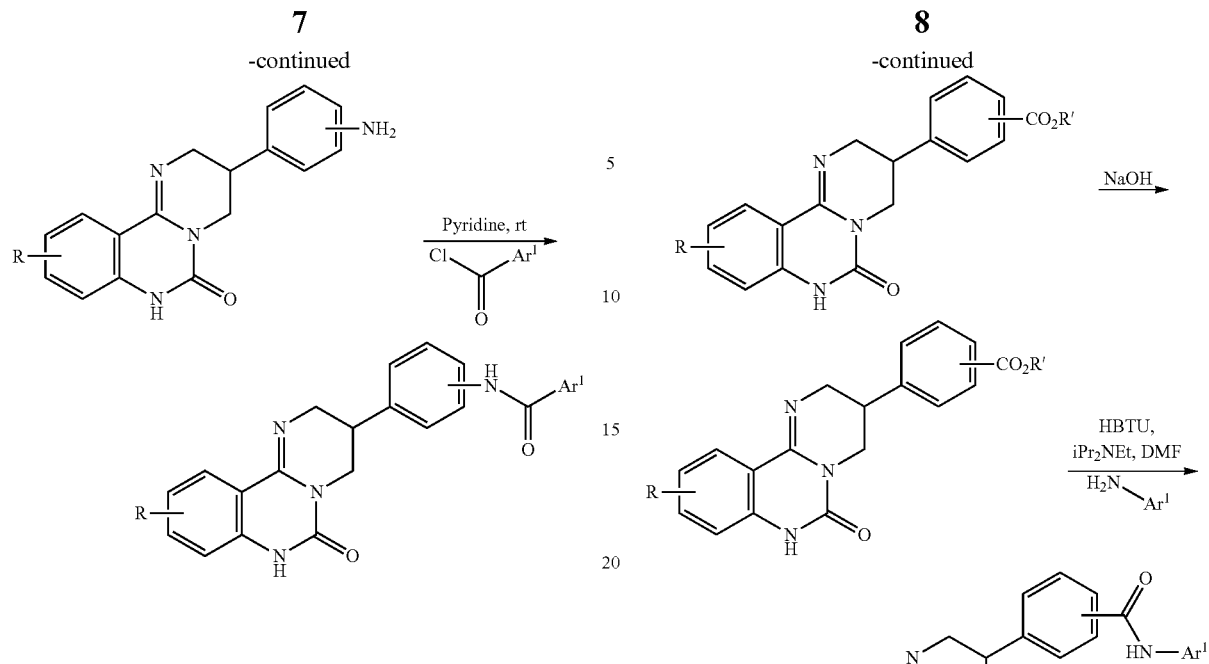
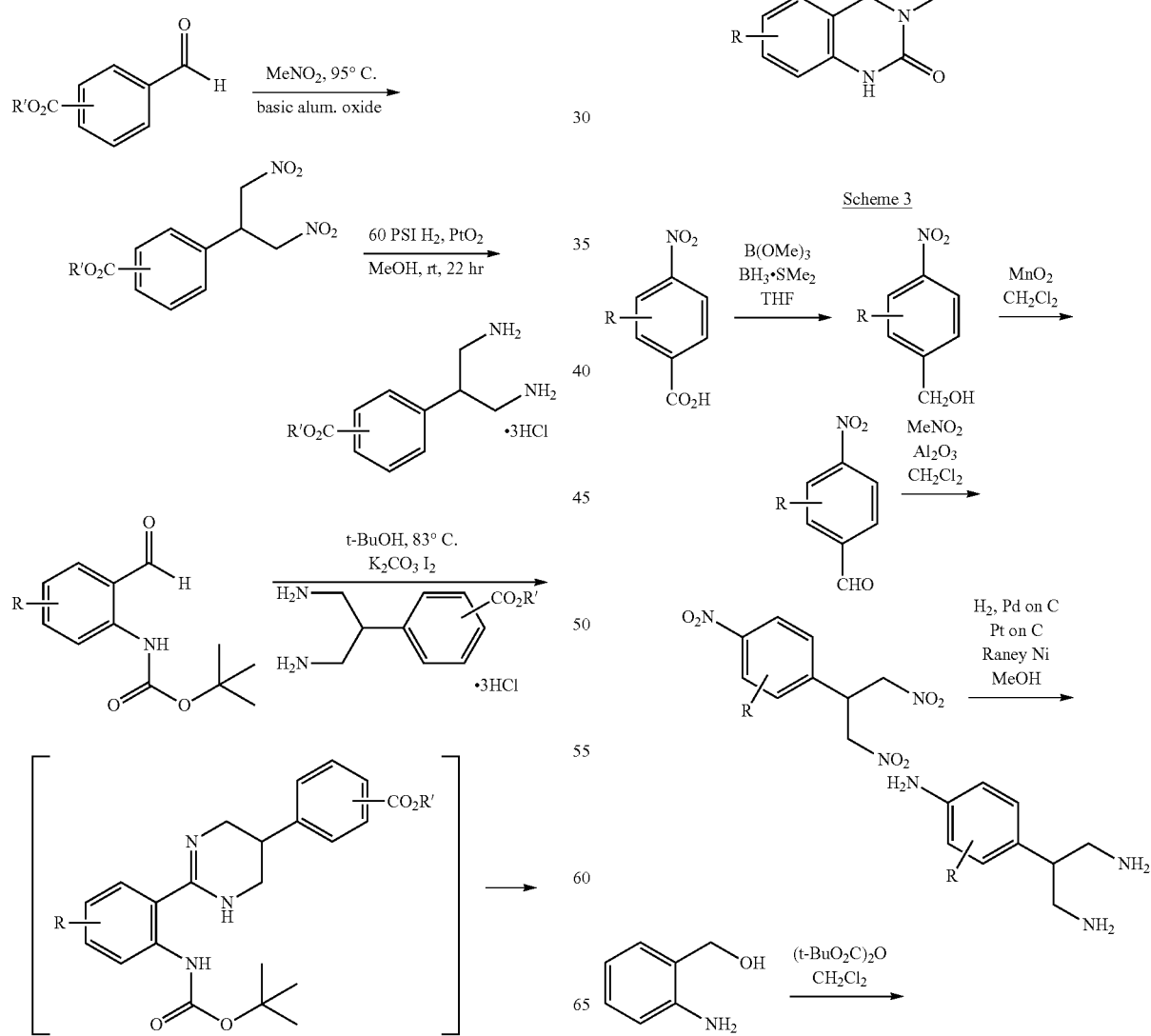

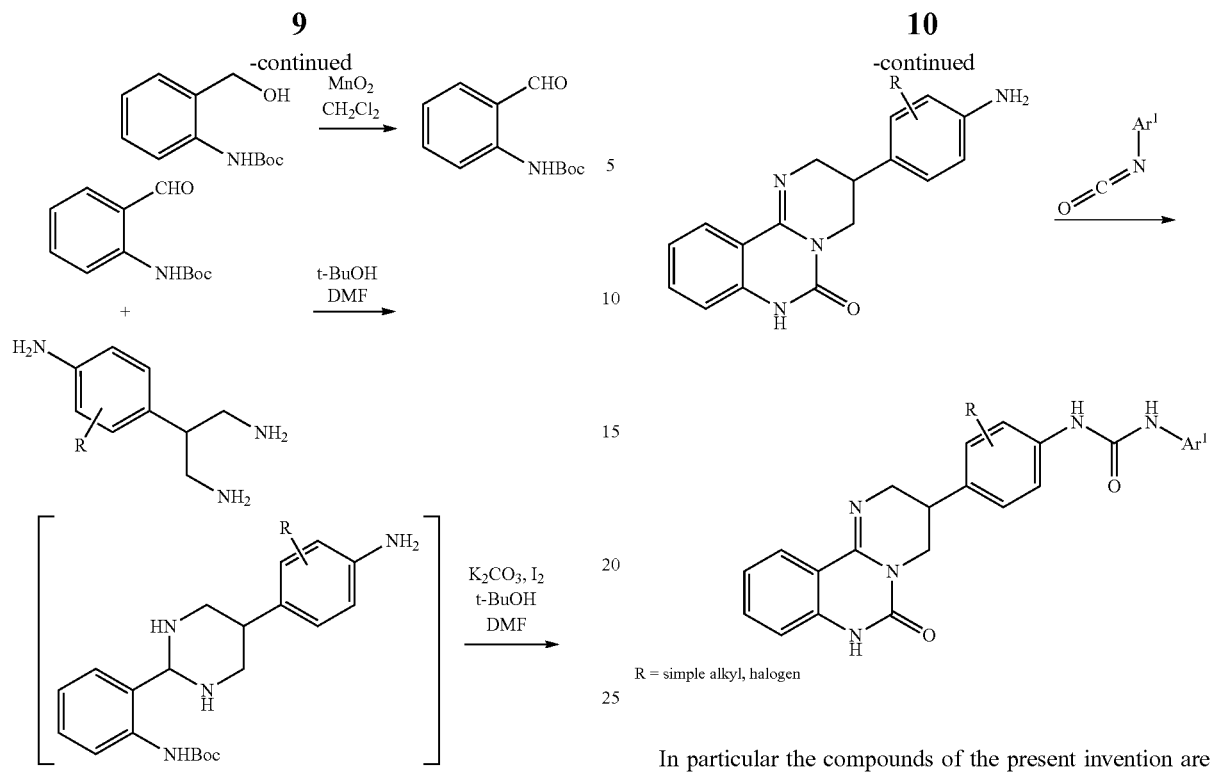
In particular the compounds of the present invention are selected from the compounds of Table 1, below.
TABLE 1
| Example Number | Structure | Compound Name |
| --- | --- | --- |
| 1 | 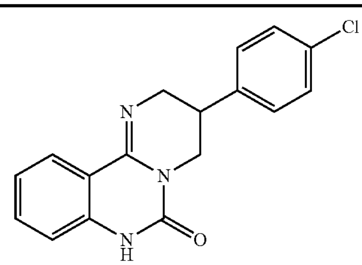 | 3-(4-chlorophenyl)-2,3,4,7-tetrahydro-6H-pyrimido[1,2-c]quinazolin-6-one |
| 2 | 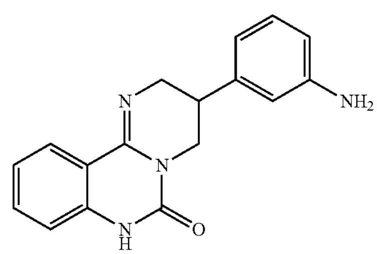 [SMILES: Nc1cccc(C2CN=C3c4ccccc4NC(=O)N3C2)c1] | 3-(3-aminophenyl)-2,3,4,7-tetrahydro-6H-pyrimido[1,2-c]quinazolin-6-one |
| 3 | 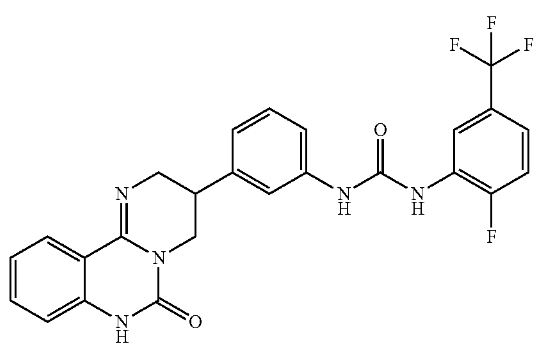 [SMILES: O=C(Nc1cccc(C2CN=C3c4ccccc4NC(=O)N3C2)c1)Nc1cc(C(F)(F)F)ccc1F] | 1-[2-fluoro-5-(trifluoromethyl)phenyl]-3-[3-(6-oxo-3,4,6,7-tetrahydro-2H-pyrimido[1,2-c]quinazolin-3-yl)phenyl]urea |

TABLE 1-continued

| Example Number | Structure | Compound Name |
|---|---|---|
| 4 | 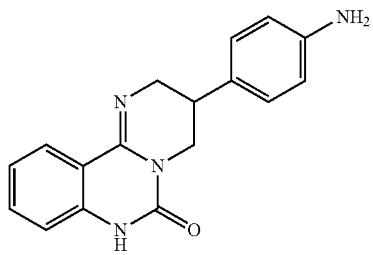 [SMILES: Nc1ccc(C2CN=C3c4ccccc4NC(=O)N3C2)cc1] | 3-(4-aminophenyl)-2,3,4,7-tetrahydro-6H-pyrimido[1,2-c]quinazolin-6-one |
| 5 | 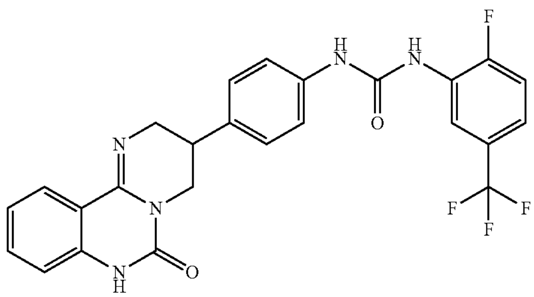 [SMILES: O=C(Nc1ccc(C2CN=C3c4ccccc4NC(=O)N3C2)cc1)Nc1cc(C(F)(F)F)ccc1F] | 1-[2-fluoro-5-(trifluoromethyl)phenyl]-3-[4-(6-oxo-3,4,6,7-tetrahydro-2H-pyrimido[1,2-c]quinazolin-3-yl)phenyl]urea |
| 6 | 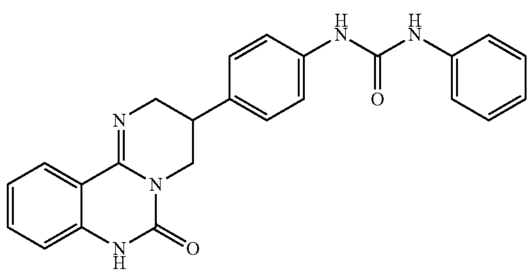 [SMILES: O=C(Nc1ccccc1)Nc1ccc(C2CN=C3c4ccccc4NC(=O)N3C2)cc1] | 1-[4-(6-oxo-3,4,6,7-tetrahydro-2H-pyrimido[1,2-c]quinazolin-3-yl)phenyl]-3-phenylurea |
| 7 | 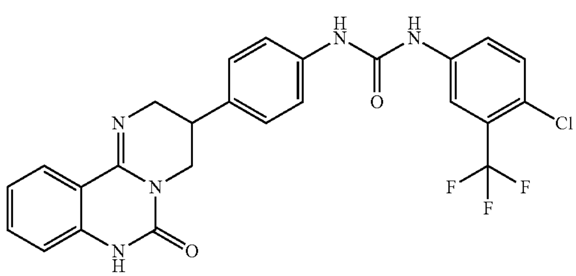 [SMILES: O=C(Nc1ccc(C2CN=C3c4ccccc4NC(=O)N3C2)cc1)Nc1ccc(Cl)c(C(F)(F)F)c1] | 1-[4-chloro-3-(trifluoromethyl)phenyl]-3-[4-(6-oxo-3,4,6,7-tetrahydro-2H-pyrimido[1,2-c]quinazolin-3-yl)phenyl]urea |
| 8 | 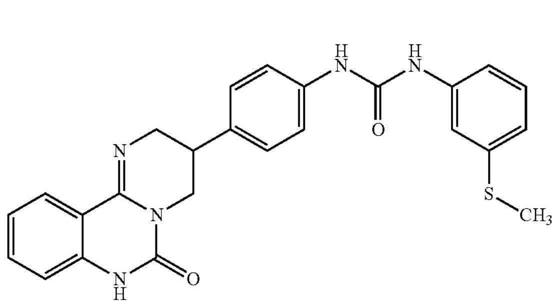 | 1-[3-(methylthio)phenyl]-3-[4-(6-oxo-3,4,6,7-tetrahydro-2H-pyrimido[1,2-c]quinazolin-3-yl)phenyl]urea |

TABLE 1-continued

| Example Number | Structure | Compound Name |
|---|---|---|
| 9 | 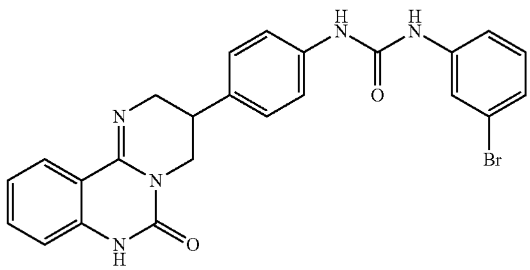 [SMILES: O=C(Nc1ccc(C2CN=C3c4ccccc4NC(=O)N3C2)cc1)Nc1cccc(Br)c1] | 1-(3-bromophenyl)-3-[4-(6-oxo-3,4,6,7-tetrahydro-2H-pyrimido[1,2-c]quinazolin-3-yl)phenyl]urea |
| 10 | 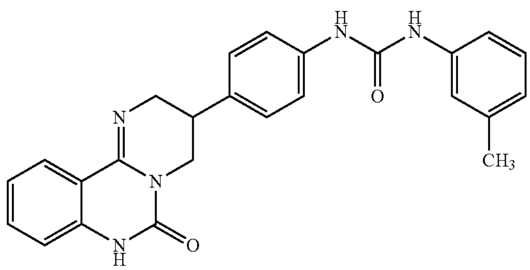 [SMILES: Cc1cccc(NC(=O)Nc2ccc(C3CN=C4c5ccccc5NC(=O)N4C3)cc2)c1] | 1-(3-methylphenyl)-3-[4-(6-oxo-3,4,6,7-tetrahydro-2H-pyrimido[1,2-c]quinazolin-3-yl)phenyl]urea |
| 11 | 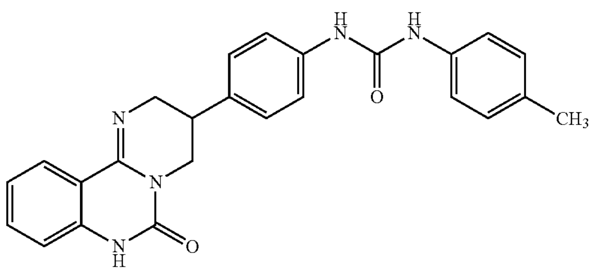 [SMILES: Cc1ccc(NC(=O)Nc2ccc(C3CN=C4c5ccccc5NC(=O)N4C3)cc2)cc1] | 1-(4-methylphenyl)-3-[4-(6-oxo-3,4,6,7-tetrahydro-2H-pyrimido[1,2-c]quinazolin-3-yl)phenyl]urea |
| 12 | 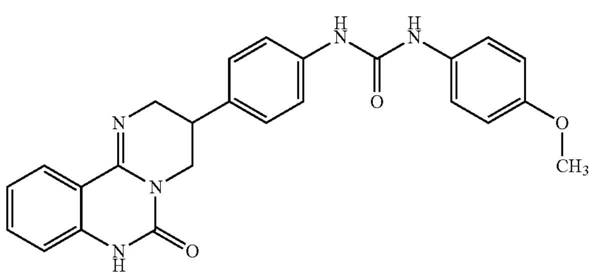 [SMILES: COc1ccc(NC(=O)Nc2ccc(C3CN=C4c5ccccc5NC(=O)N4C3)cc2)cc1] | 1-(4-methoxyphenyl)-3-[4-(6-oxo-3,4,6,7-tetrahydro-2H-pyrimido[1,2-c]quinazolin-3-yl)phenyl]urea |
| 13 | 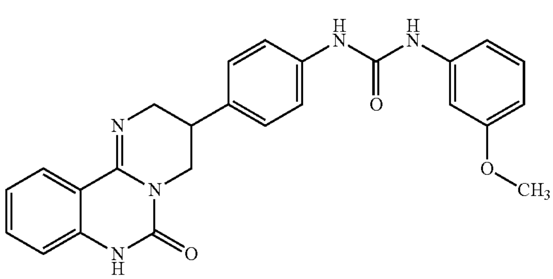 [SMILES: COc1cccc(NC(=O)Nc2ccc(C3CN=C4c5ccccc5NC(=O)N4C3)cc2)c1] | 1-(3-methoxyphenyl)-3-[4-(6-oxo-3,4,6,7-tetrahydro-2H-pyrimido[1,2-c]quinazolin-3-yl)phenyl]urea |

TABLE 1-continued

| Example Number | Structure | Compound Name |
|---|---|---|
| 14 | 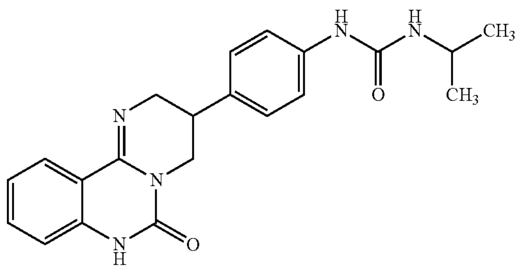 [SMILES: CC(C)NC(=O)Nc1ccc(C2CN=C3c4ccccc4NC(=O)N3C2)cc1] | 1-isopropyl-3-[4-(6-oxo-3,4,6,7-tetrahydro-2H-pyrimido[1,2-c]quinazolin-3-yl)phenyl]urea |
| 15 | 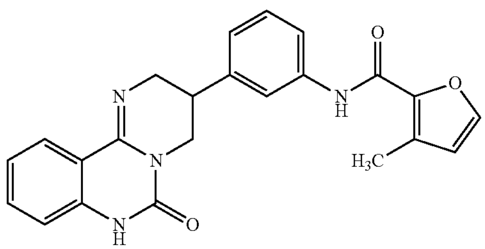 [SMILES: Cc1ccoc1C(=O)Nc1cccc(C2CN=C3c4ccccc4NC(=O)N3C2)c1] | 3-methyl-N-[3-(6-oxo-3,4,6,7-tetrahydro-2H-pyrimido[1,2-c]quinazolin-3-yl)phenyl]-2-furamide |
| 16 | 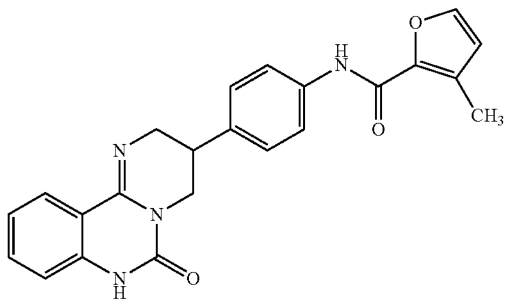 [SMILES: Cc1ccoc1C(=O)Nc1ccc(C2CN=C3c4ccccc4NC(=O)N3C2)cc1] | 3-methyl-N-[4-(6-oxo-3,4,6,7-tetrahydro-2H-pyrimido[1,2-c]quinazolin-3-yl)phenyl]-2-furamide |
| 17 | 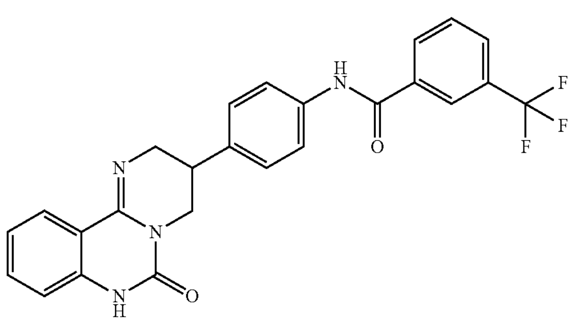 [SMILES: O=C(Nc1ccc(C2CN=C3c4ccccc4NC(=O)N3C2)cc1)c1cccc(C(F)(F)F)c1] | N-[4-(6-oxo-3,4,6,7-tetrahydro-2H-pyrimido[1,2-c]quinazolin-3-yl)phenyl]-3-(trifluoromethyl)benzamide |
| 18 | 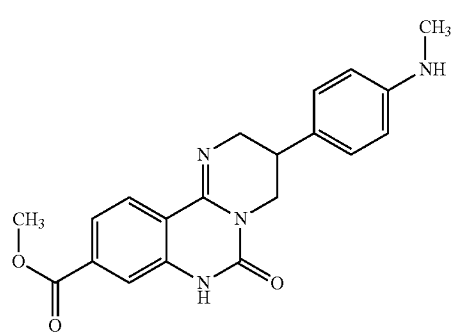 [SMILES: CNc1ccc(C2CN=C3c4ccc(C(=O)OC)cc4NC(=O)N3C2)cc1] | methyl 3-[4-(methylamino)phenyl]-6-oxo-3,4,6,7-tetrahydro-2H-pyrimido[1,2-c]quinazoline-9-carboxylate |

TABLE 1-continued

| Example Number | Structure | Compound Name |
|---|---|---|
| 19 | 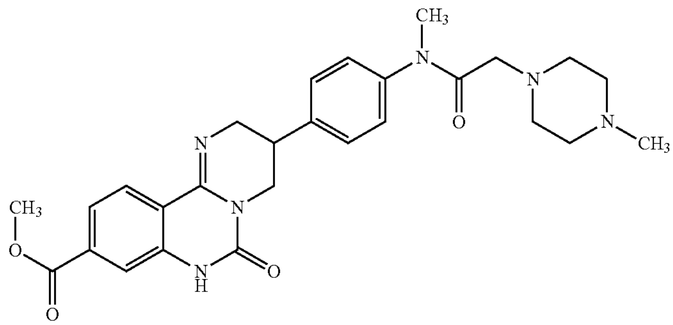 [SMILES: COC(=O)c1ccc2c(c1)NC(=O)N1CC(c3ccc(N(C)C(=O)CN4CCN(C)CC4)cc3)CN=C21] | methyl 3-(4-{methyl[(4-methylpiperazin-1-yl)acetyl]amino}phenyl)-6-oxo-3,4,6,7-tetrahydro-2H-pyrimido[1,2-c]quinazoline-9-carboxylate |
| 20 | 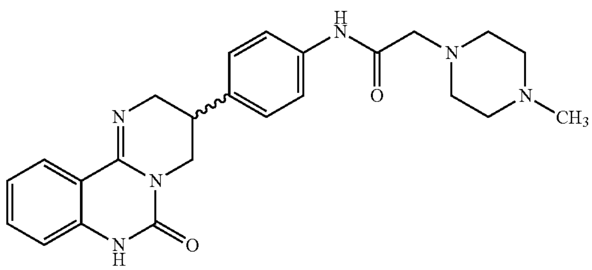 [SMILES: CN1CCN(CC(=O)Nc2ccc(C3CN=C4c5ccccc5NC(=O)N4C3)cc2)CC1] | 2-(4-methylpiperazin-1-yl)-N-[4-(6-oxo-3,4,6,7-tetrahydro-2H-pyrimido[1,2-c]quinazolin-3-yl)phenyl]acetamide |
| 21 | 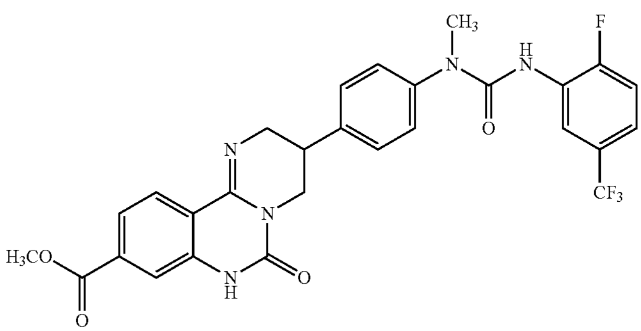 [SMILES: COC(=O)c1ccc2c(c1)NC(=O)N1CC(c3ccc(N(C)C(=O)Nc4cc(C(F)(F)F)ccc4F)cc3)CN=C21] | methyl 3-{4-[({[2-fluoro-5-(trifluoromethyl)phenyl]amino}carbonyl)(methyl)amino]phenyl}-6-oxo-3,4,6,7-tetrahydro-2H-pyrimido[1,2-c]quinazoline-9-carboxylate |
| 22 | 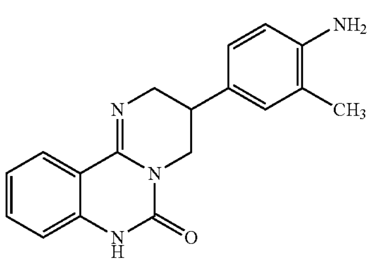 [SMILES: Cc1cc(C2CN=C3c4ccccc4NC(=O)N3C2)ccc1N] | 3-(4-amino-3-methylphenyl)-2,3,4,7-tetrahydro-6H-pyrimido[1,2-c]quinazolin-6-one |
| 23 | 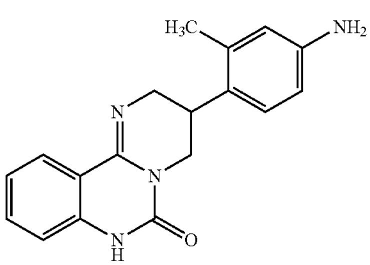 [SMILES: Cc1cc(N)ccc1C1CN=C2c3ccccc3NC(=O)N2C1] | 3-(4-amino-2-methylphenyl)-2,3,4,7-tetrahydro-6H-pyrimido[1,2-c]quinazolin-6-one |

TABLE 1-continued

| Example Number | Structure | Compound Name |
|---|---|---|
| 24 | 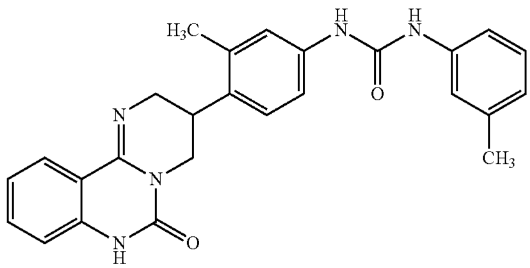 [SMILES: Cc1cccc(NC(=O)Nc2ccc(C3CN=C4c5ccccc5NC(=O)N4C3)c(C)c2)c1] | 1-[3-methyl-4-(6-oxo-3,4,6,7-tetrahydro-2H-pyrimido[1,2-c]quinazolin-3-yl)phenyl]-3-(3-methylphenyl)urea |
| 25 | 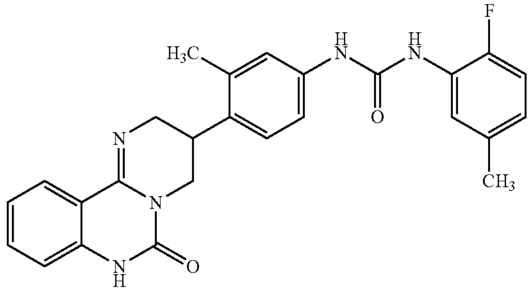 | 1-[2-fluoro-5-(trifluoromethyl)phenyl]-3-[3-methyl-4-(6-oxo-3,4,6,7-tetrahydro-2H-pyrimido[1,2-c]quinazolin-3-yl)phenyl]urea |

Biological data for the compounds of the present invention was generated by use of the following assay.

VEGFR2 Kinase Assay:

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mLs per well PBS+0.05% Tween-20 (PBS-T), blocked by incubation with PBS containing 1% BSA, then washed with 2 mLs per well PBS-T prior to starting the reaction. Reactions were carried out in 100 μL reaction volumes containing 2.7 μM ATP in kinase buffer (50 mM Hepes buffer pH 7.4, 20 mM MgCl$_2$, 0.1 mM MnCl$_2$ and 0.2 mM Na$_3$VO$_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mLs per well PBS-T. 100 μl of a monoclonal anti-phosphotyrosine antibody-peroxidase conjugate diluted 1:10,000 in PBS-T was added to the wells for 30 minutes. Following a 2 mLs per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N H$_2$SO$_4$ to each well and read using a microplate ELISA reader set at 492 nm. IC$_{50}$ values for compound inhibition were calculated directly from graphs of optical density (arbitrary units) versus compound concentration following subtraction of blank values.

TABLE 2

| Example Number | Structure | VEGFR2 Enzyme IC$_{50}$ (micromolar) |
|---|---|---|
| 1 | 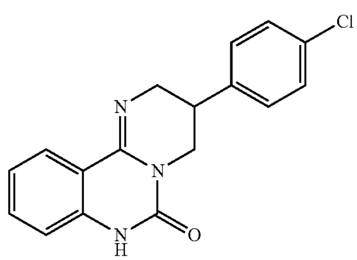 [SMILES: O=C1Nc2ccccc2C2=NCC(c3ccc(Cl)cc3)CN12] | >10 |

TABLE 2-continued

| Example Number | Structure | VEGFR2 Enzyme IC$_{50}$ (micromolar) |
|---|---|---|
| 2 | 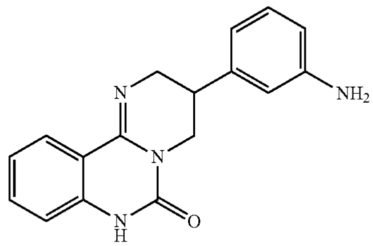 [SMILES: Nc1cccc(C2CN=C3c4ccccc4NC(=O)N3C2)c1] | >10 |
| 3 | 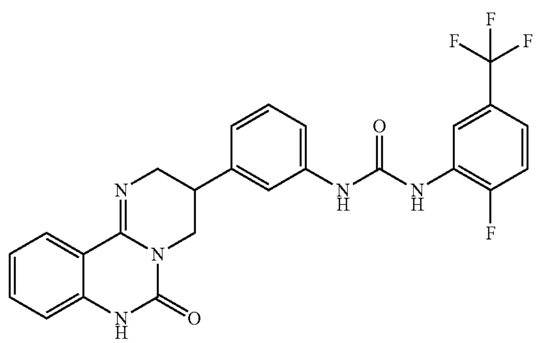 [SMILES: O=C(Nc1cccc(C2CN=C3c4ccccc4NC(=O)N3C2)c1)Nc1cc(C(F)(F)F)ccc1F] | 0.76 |
| 4 | 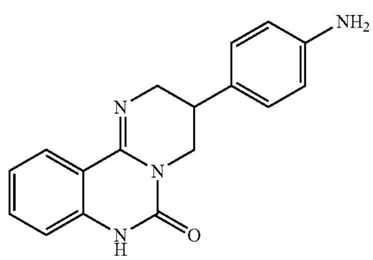 [SMILES: Nc1ccc(C2CN=C3c4ccccc4NC(=O)N3C2)cc1] | >10 |
| 5 | 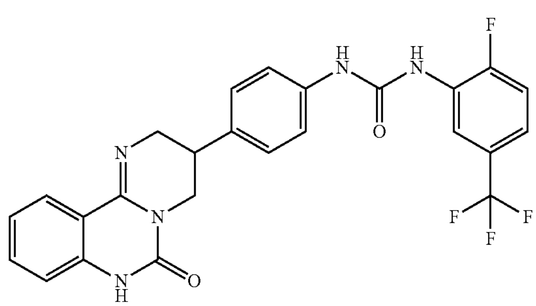 [SMILES: O=C(Nc1ccc(C2CN=C3c4ccccc4NC(=O)N3C2)cc1)Nc1cc(C(F)(F)F)ccc1F] | 0.36 |
| 6 | 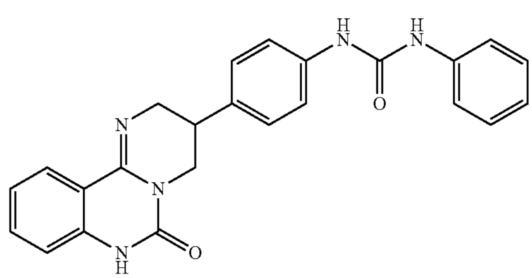 [SMILES: O=C(Nc1ccccc1)Nc1ccc(C2CN=C3c4ccccc4NC(=O)N3C2)cc1] | 4.75 |

TABLE 2-continued

| Example Number | Structure | VEGFR2 Enzyme IC$_{50}$ (micromolar) |
|---|---|---|
| 7 | 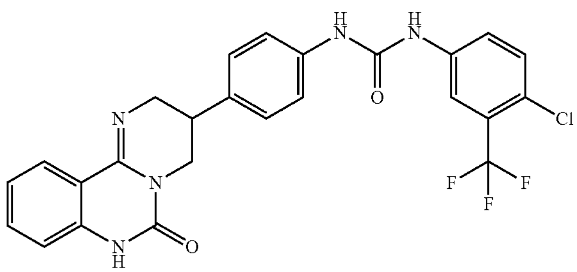 [SMILES: O=C(Nc1ccc(C2CN=C3c4ccccc4NC(=O)N3C2)cc1)Nc1ccc(Cl)c(C(F)(F)F)c1] | 0.34 |
| 8 | 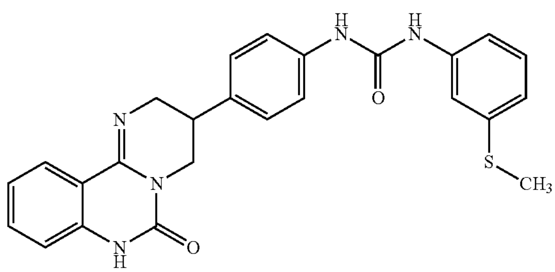 | 1.8 |
| 9 | 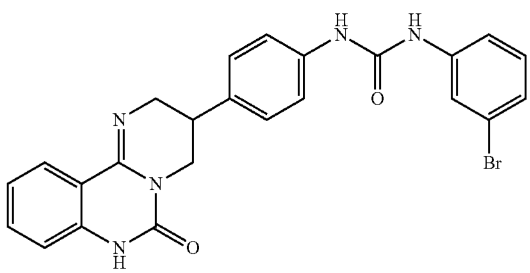 [SMILES: O=C(Nc1ccc(C2CN=C3c4ccccc4NC(=O)N3C2)cc1)Nc1cccc(Br)c1] | 0.25 |
| 10 | 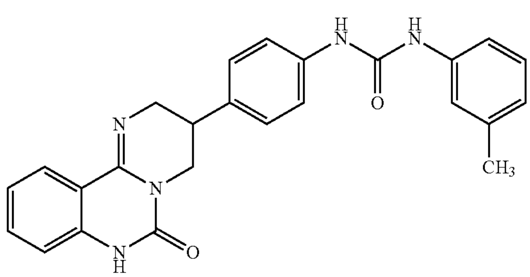 [SMILES: Cc1cccc(NC(=O)Nc2ccc(C3CN=C4c5ccccc5NC(=O)N4C3)cc2)c1] | 0.33 |
| 11 | 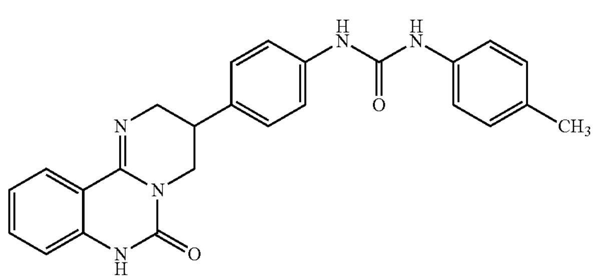 [SMILES: Cc1ccc(NC(=O)Nc2ccc(C3CN=C4c5ccccc5NC(=O)N4C3)cc2)cc1] | 4.03 |

TABLE 2-continued
| Example Number | Structure | VEGFR2 Enzyme IC$_{50}$ (micromolar) |
|---|---|---|
| 12 | 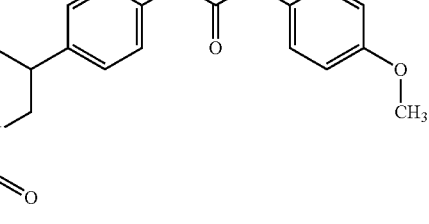 | >10 |
| 13 | 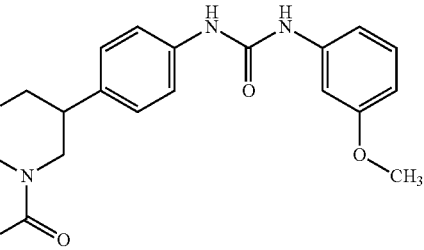 | 1.47 |
| 14 | 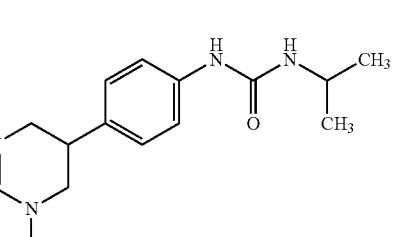 | >10 |
| 15 | 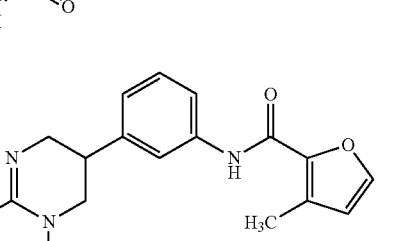 | 6.38 |
| 16 | 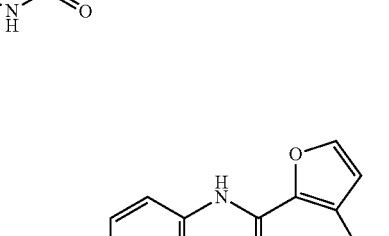 | >10 |

TABLE 2-continued

| Example Number | Structure | VEGFR2 Enzyme IC$_{50}$ (micromolar) |
| --- | --- | --- |
| 17 | 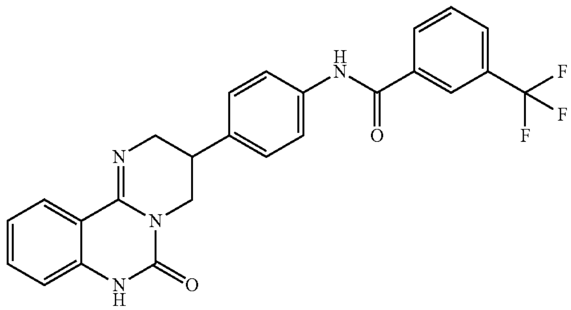 [SMILES: O=C(Nc1ccc(C2CN=C3c4ccccc4NC(=O)N3C2)cc1)c1cccc(C(F)(F)F)c1] | >10 |
| 18 | 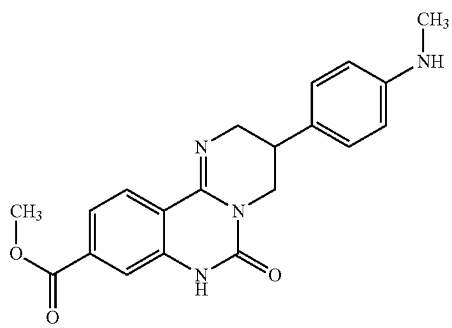 [SMILES: CNc1ccc(C2CN=C3c4ccc(C(=O)OC)cc4NC(=O)N3C2)cc1] | >10 |
| 19 | 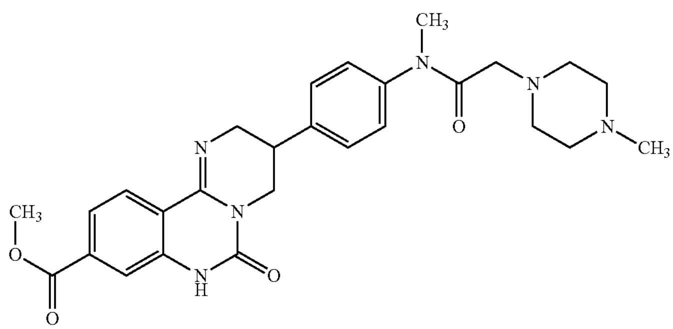 [SMILES: COC(=O)c1ccc2c(c1)NC(=O)N1CC(c3ccc(N(C)C(=O)CN4CCN(C)CC4)cc3)CN=C21] | >10 |
| 20 | 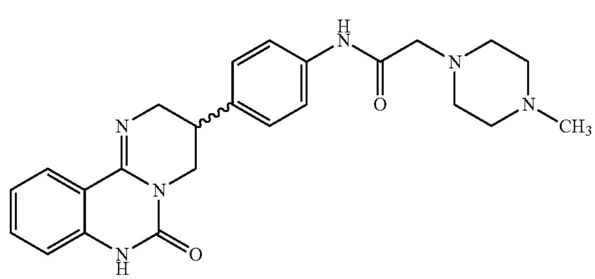 [SMILES: CN1CCN(CC(=O)Nc2ccc(C3CN=C4c5ccccc5NC(=O)N4C3)cc2)CC1] | >10 |
| 21 | 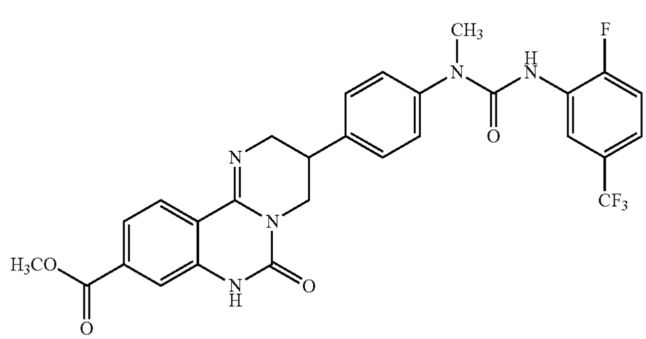 [SMILES: COC(=O)c1ccc2c(c1)NC(=O)N1CC(c3ccc(N(C)C(=O)Nc4cc(C(F)(F)F)ccc4F)cc3)CN=C21] | >10 |

TABLE 2-continued

| Example Number | Structure | VEGFR2 Enzyme IC$_{50}$ (micromolar) |
|---|---|---|
| 22 | 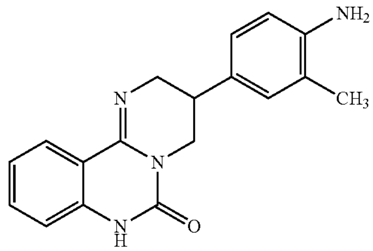 [SMILES: Cc1cc(C2CN=C3c4ccccc4NC(=O)N3C2)ccc1N] | >10 |
| 23 | 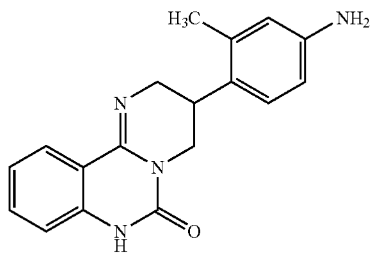 [SMILES: Cc1cc(N)ccc1C1CN=C2c3ccccc3NC(=O)N2C1] | >10 |
| 24 | 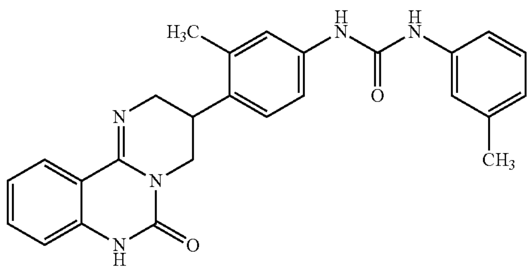 [SMILES: Cc1cccc(NC(=O)Nc2ccc(C3CN=C4c5ccccc5NC(=O)N4C3)c(C)c2)c1] | 1.5 |
| 25 | 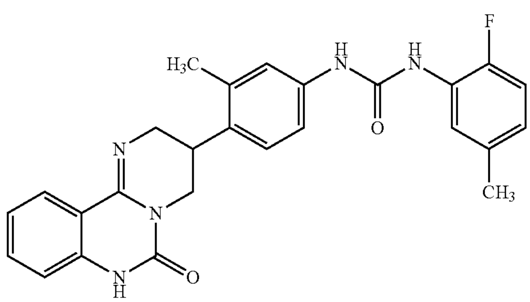 | 0.39 |

It has been, surprisingly, found from the above data that;

The compounds of Examples 3, 5, 7, 9, 10 and 15 are especially preferred as having excellent VEGFR2 potency as shown in this assay.

Also, the importance of the terminal group, i.e. Ar$^1$, being an aryl group is demonstrated by the lack of potency of the compounds of Examples 14, 19 and 20.

In the preferred compounds of the present invention, i.e. wherein n is 0, Ar is phenyl and Ar$^1$ is a substituted phenyl, the preferred substituents on the substituted phenyl are fluoro and trifluoromethyl.

The invention is further illustrated by the following non-limiting examples.

Preparation 1

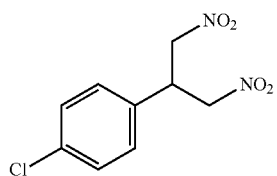 [SMILES: O=[N+]([O-])CC(C[N+](=O)[O-])c1ccc(Cl)cc1]

1-Chloro-4-[2-nitro-1-(nitromethyl)ethyl]benzene

According to the procedure described in Eur. J. Org. Chem. 2010, 3, 484-493, a mixture of 4-chlorobenzaldehyde (506 mg, 3.60 mmol) and 350 mg basic aluminum oxide in 4 mL nitromethane was heated at 95° C. After 2.5 hours the reaction mixture was cooled to rt and stirred overnight. Then reaction mixture was treated with approximately 200 mg of basic aluminum oxide and heated for 2.5 hours. The reaction mixture was filtered through a small plug of silica gel, rinsed with $CHCl_3$, and evaporated to an oil. The crude mixture was combined with 152 mg of impure product from a previous reaction and was chromatographed eluting with EtOAc/hexane to give the title compound as a tan solid (579 mg, 56% approximate yield). $^1$H NMR ($CDCl_3$) δ: 7.37 (d, J=8.5 Hz, 2H), 7.18 (d, J=8.5 Hz, 2H), 4.68-4.82 (m, 4H), 4.30 (quin, J=7.1 Hz, 1H).

Preparation 2

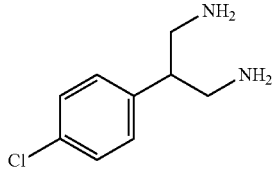 [SMILES: NCC(CN)c1ccc(Cl)cc1]

2-(4-Chlorophenyl)propane-1,3-diamine

According to the procedure described in Eur. J. Org. Chem. 2010, 3, 484-493, a mixture of 1-chloro-4-[2-nitro-1-(nitromethyl)ethyl]benzene (80 mg, 0.327 mmol) and 18 mg platinum (IV) oxide in 5 mL MeOH contained in a pressure tube was reacted under 50 PSI hydrogen. After 15 hours the mixture was filtered through Celite, rinsed with MeOH and evaporated to give a quantitative yield (60 mg) of the title compound as a yellow-orange oil. $^1$H NMR ($CD_3OD$) δ: 7.34-7.38 (m, 2H), 7.21-7.29 (m, 2H), 2.88-2.98 (m, 2H), 2.73-2.86 (m, 3H).

Preparation 3

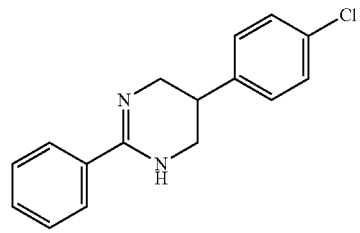 [SMILES: Clc1ccc(C2CN=C(c3ccccc3)NC2)cc1]

5-(4-Chlorophenyl)-2-phenyl-1,4,5,6-tetrahydropyrimidine

A solution of benzaldehyde (0.0056 mL, 0.056 mmol) and 2-(4-chlorophenyl)propane-1,3-diamine (10.8 mg, 0.059 mmol) in 0.7 mL t-BuOH was heated at 70° C. for 15 min. The reaction mixture was cooled to rt and treated with $K_2CO_3$ (38.5 mg, 0.279 mmol) and iodine (17.7 mg, 0.070 mmol). The reaction mixture was stirred for 5 min at rt and then heated to 70° C. for 2.5 hours. The reaction mixture was cooled to rt and saturated aqueous $Na_2SO_3$ was added dropwise until the color changed from orange to yellow. The reaction mixture was partitioned between EtOAc and aqueous $Na_2CO_3$ solution, the EtOAc layer washed with $H_2O$, brine, dried with anhydrous $Na_2SO_4$ and concentrated. The residue was chromatographed using basic aluminum oxide column and eluting with 5% MeOH/$CHCl_3$ to give the title compound as an off-white solid (13.1 mg, 87%). $^1$H NMR ($CDCl_3$) δ: 7.67-7.70 (m, 2H), 7.36-7.43 (m, 3H), 7.30-7.32 (m, 2H), 7.14-7.18 (m, 2H), 3.70 (dd, J=12.9, 4.4 Hz, 2H), 3.50 (dd, J=13.5, 10.3 Hz, 2H), 3.00 (tt, J=10.0, 4.8 Hz, 1H).

Example 1

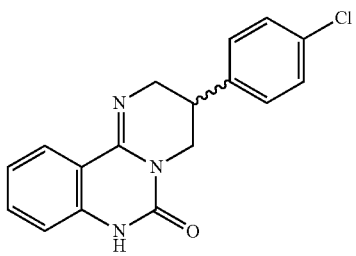 [SMILES: O=C1Nc2ccccc2C2=NCC(c3ccc(Cl)cc3)CN12]

3-(4-Chlorophenyl)-2,3,4,7-tetrahydro-6H-pyrimido[1,2-c]quinazolin-6-one

A mixture of 5-(4-chlorophenyl)-2-phenyl-1,4,5,6-tetrahydropyrimidine (12.9 mg, 0.048 mmol), tert-butyl carbamate (16.7 mg, 0.143 mmol) and copper(II) acetate (8.7 mg, 0.048 mmol) in 0.6 mL DMF was heated at 100° C. in a sealed reaction vessel under an oxygen gas atmosphere. After 1 hour the DMF solvent was evaporated and the residue chromatographed eluting with 5% MeOH/$CHCl_3$ to give the title compound as a pale yellow solid (1.8 mg, 12%). $^1$H NMR (Acetone-d6) δ: 9.54 (br. s, 1H), 8.10 (d, J=7.9 Hz, 1H), 7.36-7.49 (m, 5H), 7.05-7.13 (m, 2H), 4.32-4.41 (m, 1H), 3.79-3.89 (m, 1H), 3.54-3.71 (m, 2H), 3.05-3.20 (m, 1H).

Preparation 4

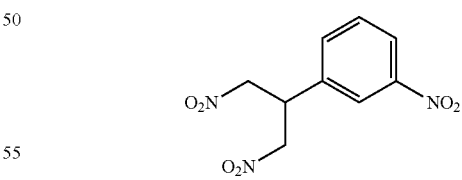

1-Nitro-3-[2-nitro-1-(nitromethyl)ethyl]benzene

A mixture of 3-nitrobenzaldehyde (907 mg, 6.0 mmol) and 1.0 g basic aluminum oxide in 10 mL nitromethane was heated at 95° C. After 3 hours the mixture was filtered, rinsed with $CHCl_3$ and concentrated. The residue was chromatographed through a plug of silica gel eluting with $CHCl_3$/EtOAc to give the title compound as an orange-tan solid (1.246 g, 81%). $^1$H NMR (DMSO-d6) δ: 8.40 (t, J=2.1 Hz, 1H), 8.18 (ddd, J=8.3, 2.3, 1.2 Hz, 1H), 7.90 (dt, J=7.7, 1.4 Hz, 1H), 7.64-7.71 (m, 1H), 5.02-5.19 (m, 4H), 4.44 (tt, J=8.5, 6.3 Hz, 1H).

Preparation 5

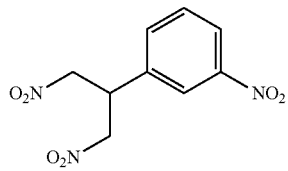 [SMILES: O=[N+]([O-])CC(C[N+](=O)[O-])c1cccc([N+](=O)[O-])c1]

2-(3-Aminophenyl)propane-1,3-diamine

A mixture of 1-nitro-3-[2-nitro-1-(nitromethyl)ethyl]benzene (115 mg, 0.45 mmol) and 58 mg platinum (IV) oxide in 6 mL MeOH contained in a pressure tube was reacted under 65 PSI hydrogen. After 16 hours the mixture was filtered and rinsed with MeOH. The MeOH solution of product was stored under $N_2$ in the freezer and used as is for the next reaction [upon evaporation of MeOH solvent 69.9 mg (94%) of the title compound was obtained as a light yellow oil]. $^1$H NMR (CD$_3$OD) δ: 7.06-7.13 (m, 1H), 6.55-6.65 (m, 3H), 2.83-2.91 (m, 2H), 2.72-2.81 (m, 2H), 2.57-2.68 (m, 1H).

Example 2

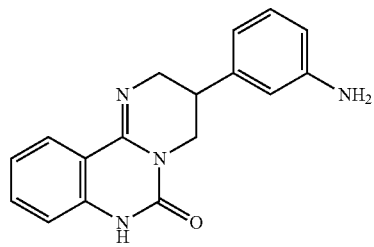 [SMILES: Nc1cccc(C2CN=C3c4ccccc4NC(=O)N3C2)c1]

3-(3-Aminophenyl)-2,3,4,7-tetrahydro-6H-pyrimido[1,2-c]quinazolin-6-one

The MeOH solution of 2-(3-aminophenyl)propane-1,3-diamine was evaporated just prior to use, then chased with 1 mL t-BuOH to give a light yellow oil (31 mg, 0.188 mmol). To this was added tert-butyl(2-formylphenyl)carbamate (41.5 mg, 0.188 mmol), powdered K$_2$CO$_3$ (104 mg, 0.75 mmol) and 1.2 mL t-BuOH. The reaction mixture heated at 80° C. for 2.25 hours and then cooled to rt. The reaction mixture was treated with iodine (48 mg, 0.188 mmol), stirred 5 min at rt and then the reaction heated at 80° C. for 1 hour. The reaction was cooled to rt and partitioned between EtOAc and aqueous Na$_2$CO$_3$ solution plus Na$_2$S$_2$O$_3$. The EtOAc layer washed with brine, dried with Na$_2$SO$_4$, and concentrated. The resulting solid was chromatographed eluting with CHCl$_3$/MeOH. The residue was then triturated with hot EtOAc to give the title compound as an off-white solid (31.3 mg, 57%). $^1$H NMR (CD$_3$OD/CDCl$_3$ mixture) δ: 8.02 (dd, J=7.9, 1.2 Hz, 1H), 7.46 (ddd, J=8.1, 7.1, 1.5 Hz, 1H), 7.10-7.17 (m, 2H), 7.00-7.04 (m, 1H), 6.63-6.69 (m, 3H), 4.41-4.49 (m, 1H), 3.80-3.89 (m, 1H), 3.53-3.66 (m, 2H), 2.98 (tt, J=10.8, 4.4 Hz, 1H).

Example 3

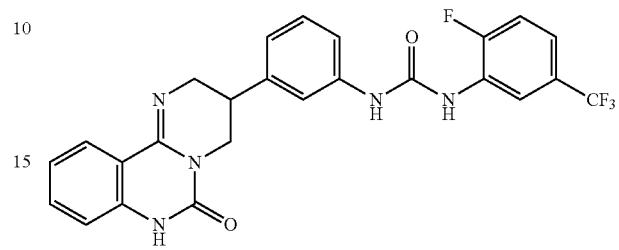

1-[2-Fluoro-5-(trifluoromethyl)phenyl]-3-[3-(6-oxo-3,4,6,7-tetrahydro-2H-pyrimido[1,2-c]quinazolin-3-yl)phenyl]urea To a solution of 3-(3-aminophenyl)-2,3,4,7-tetrahydro-6H-pyrimido[1,2-c]quinazolin-6-one (12.2 mg, 0.042 mmol) in 0.9 mL THF was added 2-fluoro-5-(trifluoromethyl)phenyl isocyanate (0.0066 mL, 0.046 mmol) and the reaction stirred at rt. After 15 min, the reaction was briefly warmed to approximately 50° C. and then allowed to cool to rt. At 40 min the reaction was quenched with 1 mL MeOH, evaporated, and chromatographed eluting with 2% to 5% MeOH/CHCl$_3$ gradient. The resulting solid was triturated with 40% EtOAc/hexane to give the title compound as a light tan solid (9.9 mg, 48%). $^1$H NMR (Acetone-d6) δ: 9.54 (br. s, 1H), 8.77-8.81 (m, 1H), 8.66 (s, 1H), 8.34 (d, J=2.9 Hz, 1H), 8.09-8.13 (m, 1H), 7.29-7.54 (m, 6H), 7.03-7.12 (m, 3H), 4.41 (ddd, J=12.9, 4.4, 2.9 Hz, 1H), 3.81-3.90 (m, 1H), 3.56-3.70 (m, 2H), 3.02-3.14 (m, 1H).

Preparation 6

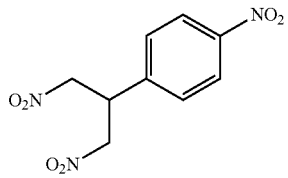 [SMILES: O=[N+]([O-])CC(C[N+](=O)[O-])c1ccc([N+](=O)[O-])cc1]

1-Nitro-4-[2-nitro-1-(nitromethyl)ethyl]benzene

According to the procedure described in Synthesis 2004, 1938-1940, a mixture of 4-nitrobenzaldehyde (907 mg, 6.0 mmol) and 1.0 g basic aluminum oxide in 10 mL nitromethane was heated at 95° C. After 3 hours the mixture was filtered, rinsed with CHCl$_3$, and concentrated. The residue was chromatographed through a plug of silica gel eluting with CHCl$_3$/EtOAc and then crystallized from EtOAc/hexane to give the title compound as an orange solid (783 mg, 51%).

¹H NMR (DMSO-d6) δ: 8.23 (d, J=8.8 Hz, 2H), 7.74 (d, J=8.8 Hz, 2H), 5.10-5.19 (m, 2H), 4.99-5.10 (m, 2H), 4.34-4.48 (m, 1H).

Preparation 7

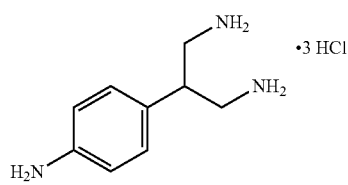

2-(4-Aminophenyl)propane-1,3-diamine.3HCl

A mixture of 1-nitro-4-[2-nitro-1-(nitromethyl)ethyl]benzene (742 mg, 0.45 mmol) and 148 mg platinum (IV) oxide in 40 mL MeOH was reacted under 60 PSI hydrogen on the Pan apparatus. After 24 hours the mixture was filtered and rinsed with MeOH. The MeOH solution was acidified to pH=0 using concentrated HCl and then evaporated to give a quantitative yield of the title compound. ¹H NMR (D₂O) δ: 7.55-7.60 (m, 2H), 7.48-7.54 (m, 2H), 3.26-3.51 (m, 5H).

Example 4

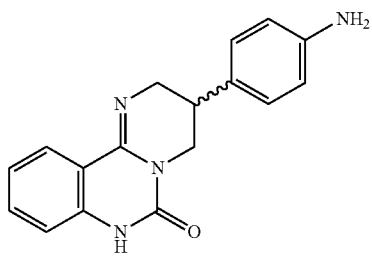 [SMILES: Nc1ccc(C2CN=C3c4ccccc4NC(=O)N3C2)cc1]

3-(4-Aminophenyl)-2,3,4,7-tetrahydro-6H-pyrimido[1,2-c]quinazolin-6-one

A mixture of 2-(4-aminophenyl)propane-1,3-diamine.3HCl (632 mg, 2.30 mmol) and powdered K₂CO₃ (3.18 g, 23.0 mmol) in 30 mL t-BuOH was heated at 83° C. for 45 min, then tert-butyl(2-formylphenyl)carbamate (560 mg, 2.53 mmol) was added. At 6.5 hours the reaction was allowed to partially cool, approximately 25 mg tert-butyl(2-formylphenyl)carbamate was added, then iodine (48 mg, 0.188 mmol) added, stirred 5 min at rt, and the heating resumed at 83° C. After 1.5 hours the temperature was lowered to 75° C. and the reaction continued an additional 15 hours. The reaction was partitioned between EtOAc and aqueous Na₂CO₃ solution plus Na₂S₂O₃, the EtOAc layer washed with brine, dried with Na₂SO₄, and evaporated. The resulting solid was chromatographed eluting with CHCl₃/MeOH to give the title compound as a yellow-tan solid (262 mg, 39%). ¹H NMR (DMSO-d6) δ: 10.65 (br. s, 1H), 7.97 (dd, J=7.9, 1.5 Hz, 1H), 7.39-7.45 (m, 1H), 6.98-7.08 (m, 2H), 6.93-6.98 (m, 2H), 6.51-6.57 (m, 2H), 4.96 (br. s, 2H), 4.12-4.20 (m, 1H), 3.61-3.70 (m, 1H), 3.36-3.53 (m, 2H), 2.73-2.85 (m, 1H).

Example 5

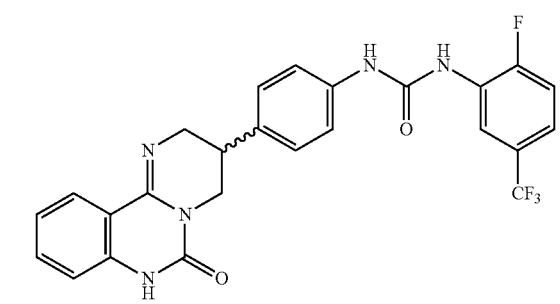 [SMILES: O=C(Nc1ccc(C2CN=C3c4ccccc4NC(=O)N3C2)cc1)Nc1cc(C(F)(F)F)ccc1F]

1-[2-Fluoro-5-(trifluoromethyl)phenyl]-3-[4-(6-oxo-3,4,6,7-tetrahydro-2H-pyrimido[1,2-c]quinazolin-3-yl)phenyl]urea To a solution of 3-(4-aminophenyl)-2,3,4,7-tetrahydro-6H-pyrimido[1,2-c]quinazolin-6-one (6.1 mg, 0.021 mmol) in 0.7 mL THF was added 2-fluoro-5-(trifluoromethyl)phenyl isocyanate (0.0033 mL, 0.023 mmol) and the reaction stirred at rt. After 1 hour the reaction was quenched with MeOH, evaporated, triturated with hot EtOAc, hexane added, and the solid filtered to give the title compound as a white solid (8.8 mg, 85%). ¹H NMR (Acetone-d6) δ: 9.54 (br. s, 1H), 8.77-8.82 (m, 1H), 8.63 (br. s, 1H), 8.33 (d, J=3.2 Hz, 1H), 8.09-8.13 (m, 1H), 7.54-7.59 (m, 2H), 7.29-7.48 (m, 5H), 7.06-7.12 (m, 2H), 4.34-4.42 (m, 1H), 3.79-3.87 (m, 1H), 3.54-3.69 (m, 2H), 3.00-3.11 (m, 1H).

Example 6

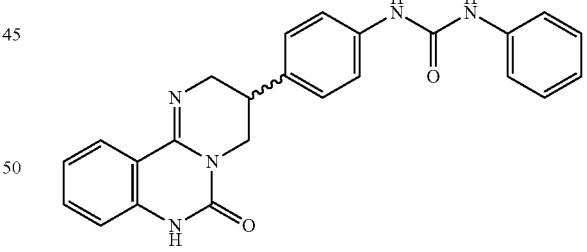

1-[4-(6-Oxo-3,4,6,7-tetrahydro-2H-pyrimido[1,2-c]quinazolin-3-yl)phenyl]-3-phenylurea To a mixture of 3-(4-aminophenyl)-2,3,4,7-tetrahydro-6H-pyrimido[1,2-c]quinazolin-6-one (25.1 mg, 0.086 mmol) in 1.1 mL THF was added phenyl isocyanate (0.0103 mL, 0.095 mmol) and the reaction stirred at rt. After 45 min, the reaction was briefly warmed to approximately 50° C. and then allowed to cool to rt. At 2.5 hours the reaction was quenched with MeOH, evaporated, then triturated with MeOH, EtOAc, and then 50% EtOAc/hexane to give the title compound as a light tan solid (25.0 mg, 71%). ¹H NMR (DMSO-d6) δ: 10.69 (br.

s, 1H), 8.64 (br. s, 2H), 7.98 (d, J=7.0 Hz, 1H), 7.40-7.47 (m, 5H), 7.21-7.31 (m, 4H), 6.92-7.10 (m, 3H), 4.18-4.26 (m, 1H), 3.67-3.77 (m, 1H), 3.49-3.61 (m, 2H), 2.89-3.03 (m, 1H).

Example 7

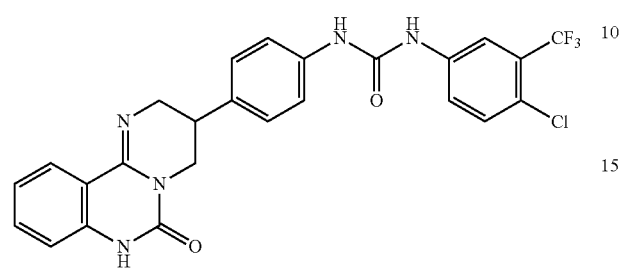

1-[4-Chloro-3-(trifluoromethyl)phenyl]-3-[4-(6-oxo-3,4,6,7-tetrahydro-2H-pyrimido[1,2-c]quinazolin-3-yl)phenyl]urea To a solution of 3-(4-aminophenyl)-2,3,4,7-tetrahydro-6H-pyrimido[1,2-c]quinazolin-6-one (20.2 mg, 0.069 mmol) in 1.6 mL THF was added 4-chloro-3-(trifluoromethyl)phenyl isocyanate (16.8 mg, 0.076 mmol) and the reaction stirred at rt. After 45 min, the reaction was briefly warmed to approximately 50° C. and then allowed to cool to rt. After 1.5 hours the stirring was stopped and the reaction left to stand at rt overnight. Then using a stream of nitrogen and gentle heating, the THF was evaporated to 1 mL, let mixture stand for 30 minutes, then filtered and rinsed with 50% EtOAc in hexane to give the title compound as an off-white solid (20.9 mg, 59%). $^1$H NMR (DMSO-d6) δ: 10.69 (br. s, 1H), 9.14 (br. s, 1H), 8.82 (br. s, 1H), 8.10 (d, J=2.3 Hz, 1H), 7.97-7.99 (m, 1H), 7.59-7.65 (m, 2H), 7.42-7.45 (m, 3H), 7.26 (d, J=8.8 Hz, 2H), 7.05-7.08 (m, 1H), 7.01 (d, J=7.9 Hz, 1H), 4.20-4.24 (m, 1H), 3.70-3.75 (m, 1H), 3.52-3.59 (m, 2H), 2.94-3.01 (m, 1H).

Example 8

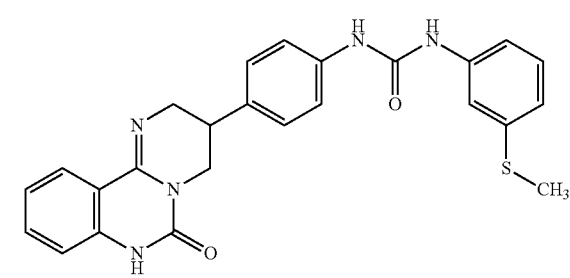 [SMILES: CSc1cccc(NC(=O)Nc2ccc(C3CN=C4c5ccccc5NC(=O)N4C3)cc2)c1]

1-[3-(Methylthio)phenyl]-3-[4-(6-oxo-3,4,6,7-tetrahydro-2H-pyrimido[1,2-c]quinazolin-3-yl)phenyl]urea In a manner similar to the procedure described in Example 7, 3-(4-aminophenyl)-2,3,4,7-tetrahydro-6H-pyrimido[1,2-c]quinazolin-6-one (20.2 mg, 0.069 mmol) and 3-(methylthio)phenyl isocyanate (0.0105 mL, 0.076 mmol) were reacted to give the title compound as an off-white solid (14.8 mg, 47%). $^1$H NMR (DMSO-d6) δ: 10.68 (s, 1H), 8.69 (s, 1H), 8.66 (s, 1H), 7.98 (d, J=7.9 Hz, 1H), 7.41-7.47 (m, 4H), 7.19-7.26 (m, 3H), 7.13-7.15 (m, 1H), 7.06 (t, J=7.5 Hz, 1H), 7.01 (d, J=7.9 Hz, 1H), 6.84-6.87 (m, 1H), 4.22 (dt, J=12.7, 3.0 Hz, 1H), 3.70-3.75 (m, 1H), 3.51-3.59 (m, 2H), 2.93-2.99 (m, 1H), 2.45 (s, 3H).

Example 9

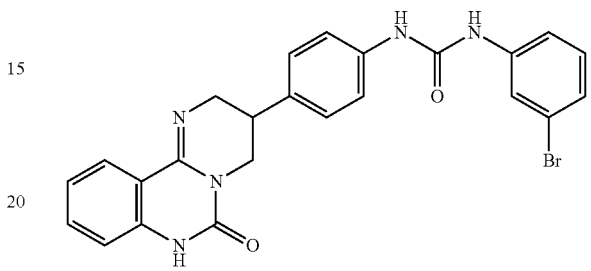

1-(3-Bromophenyl)-3-[4-(6-oxo-3,4,6,7-tetrahydro-2H-pyrimido[1,2-c]quinazolin-3-yl)phenyl]urea In a manner similar to the procedure described in Example 7, 3-(4-aminophenyl)-2,3,4,7-tetrahydro-6H-pyrimido[1,2-c]quinazolin-6-one (20.2 mg, 0.069 mmol) and 3-bromophenyl isocyanate (0.0095 mL, 0.076 mmol) were reacted to give the title compound as an off-white solid (22.4 mg, 66%). $^1$H NMR (DMSO-d6) δ: 10.69 (s, 1H), 8.85 (s, 1H), 8.72 (s, 1H), 7.97-7.99 (m, 1H), 7.85 (t, J=1.9 Hz, 1H), 7.42-7.45 (m, 3H), 7.29-7.31 (m, 1H), 7.21-7.27 (m, 3H), 7.13-7.15 (m, 1H), 7.05-7.08 (m, 1H), 7.01 (d, J=7.9 Hz, 1H), 4.20-4.24 (m, 1H), 3.70-3.75 (m, 1H), 3.52-3.59 (m, 2H), 2.94-3.00 (m, 1H).

Example 10

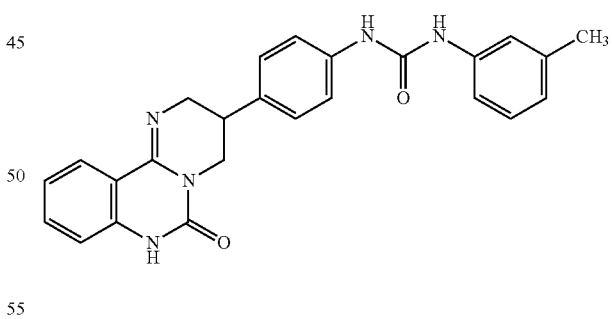

1-(3-Methylphenyl)-3-[4-(6-oxo-3,4,6,7-tetrahydro-2H-pyrimido[1,2-c]quinazolin-3-yl)phenyl]urea In a manner similar to the procedure described in Example 7, 3-(4-aminophenyl)-2,3,4,7-tetrahydro-6H-pyrimido[1,2-c]quinazolin-6-one (20.2 mg, 0.069 mmol) and meta-tolyl isocyanate (0.0095 mL, 0.076 mmol) were reacted to give the title compound as a pale tan solid (21.6 mg, 73%). $^1$H NMR (DMSO-d6) δ: 10.68 (br. s, 1H), 8.63 (s, 1H), 8.57 (s, 1H), 7.98 (dd, J=7.9, 1.2 Hz, 1H), 7.41-7.45 (m, 3H), 7.29 (s, 1H), 7.21-7.25 (m, 3H), 7.13-7.16 (m, 1H), 7.05-7.08 (m, 1H), 7.02 (d, J=7.9 Hz, 1H), 6.78 (d, J=7.3 Hz, 1H), 4.20-4.24 (m, 1H), 3.70-3.75 (m, 1H), 3.51-3.59 (m, 2H), 2.93-2.99 (m, 1H), 2.27 (s, 3H).

Example 11

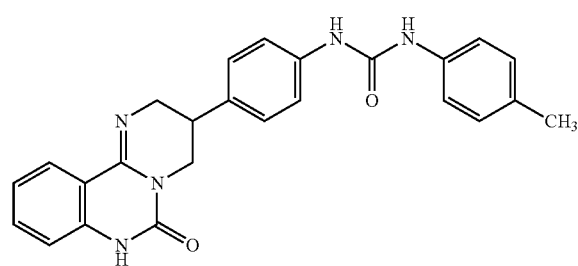 [SMILES: Cc1ccc(NC(=O)Nc2ccc(C3CN=C4c5ccccc5NC(=O)N4C3)cc2)cc1]

1-(4-Methylphenyl)-3-[4-(6-oxo-3,4,6,7-tetrahydro-2H-pyrimido[1,2-c]quinazolin-3-yl)phenyl]urea In a manner similar to the procedure described in Example 7, 3-(4-aminophenyl)-2,3,4,7-tetrahydro-6H-pyrimido[1,2-c]quinazolin-6-one (20.2 mg, 0.069 mmol) and para-tolyl isocyanate (0.0096 mL, 0.076 mmol) were reacted to give the title compound as a pale tan solid (25.5 mg, 87%). $^{1}$H NMR (DMSO-d6) δ: 10.68 (s, 1H), 8.59 (s, 1H), 8.53 (s, 1H), 7.98 (d, J=7.9 Hz, 1H), 7.40-7.45 (m, 3H), 7.33 (d, J=8.2 Hz, 2H), 7.23 (d, J=8.5 Hz, 2H), 7.05-7.09 (m, 3H), 7.01 (d, J=8.2 Hz, 1H), 4.22 (dt, J=12.6, 3.5 Hz, 1H), 3.72 (dt, J=16.0, 3.4 Hz, 1H), 3.51-3.59 (m, 2H), 2.92-2.99 (m, 1H), 2.24 (s, 3H).

Example 12

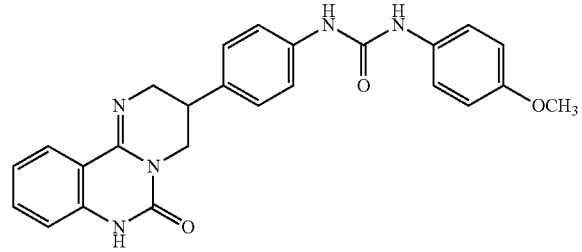 [SMILES: COc1ccc(NC(=O)Nc2ccc(C3CN=C4c5ccccc5NC(=O)N4C3)cc2)cc1]

1-(4-Methoxyphenyl)-3-[4-(6-oxo-3,4,6,7-tetrahydro-2H-pyrimido[1,2-c]quinazolin-3-yl)phenyl]urea In a manner similar to the procedure described in Example 7, 3-(4-aminophenyl)-2,3,4,7-tetrahydro-6H-pyrimido[1,2-c]quinazolin-6-one (20.2 mg, 0.069 mmol) and 4-methoxyphenyl isocyanate (0.0098 mL, 0.076 mmol) were reacted to give the title compound as an off-white solid (24.8 mg, 81%). $^{1}$H NMR (DMSO-d6) δ: 10.68 (s, 1H), 8.55 (s, 1H), 8.44 (s, 1H), 7.98 (d, J=7.0 Hz, 1H), 7.40-7.45 (m, 3H), 7.33-7.36 (m, 2H), 7.22 (d, J=8.5 Hz, 2H), 7.06 (t, J=7.6 Hz, 1H), 7.01 (d, J=8.2 Hz, 1H), 6.85-6.88 (m, 2H), 4.22 (dt, J=12.6, 3.5 Hz, 1H), 3.69-3.75 (m, 4H), 3.50-3.58 (m, 2H), 2.92-2.99 (m, 1H).

Example 13

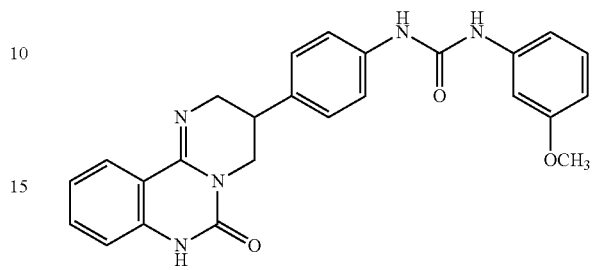

1-(3-Methoxyphenyl)-3-[4-(6-oxo-3,4,6,7-tetrahydro-2H-pyrimido[1,2-c]quinazolin-3-yl)phenyl]urea In a manner similar to the procedure described in Example 7, 3-(4-aminophenyl)-2,3,4,7-tetrahydro-6H-pyrimido[1,2-c]quinazolin-6-one (20.2 mg, 0.069 mmol) and 3-methoxyphenyl isocyanate (0.0098 mL, 0.076 mmol) were reacted to give the title compound as a white solid (20.1 mg, 66%). $^{1}$H NMR (DMSO-d6) δ: 10.69 (s, 1H), 8.65 (s, 1H), 8.62 (s, 1H), 7.98 (d, J=7.3 Hz, 1H), 7.39-7.47 (m, 3H), 7.13-7.27 (m, 4H), 6.98-7.10 (m, 2H), 6.93 (d, J=7.6 Hz, 1H), 6.55 (dd, J=8.4, 2.2 Hz, 1H), 4.18-4.26 (m, 1H), 3.73 (s, 4H), 3.48-3.62 (m, 2H), 2.90-3.02 (m, 1H).

Example 14

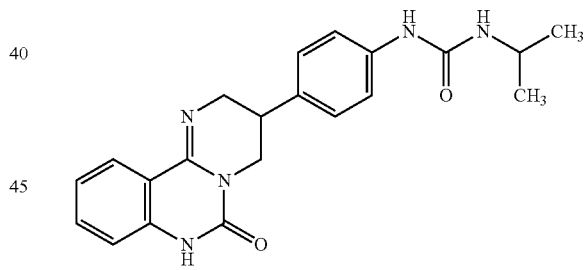

1-Isopropyl-3-[4-(6-oxo-3,4,6,7-tetrahydro-2H-pyrimido[1,2-c]quinazolin-3-yl)phenyl]urea To a solution of 3-(4-aminophenyl)-2,3,4,7-tetrahydro-6H-pyrimido[1,2-c]quinazolin-6-one (20.2 mg, 0.069 mmol) in 1.6 mL THF was added isopropyl isocyanate (0.0074 mL, 0.076 mmol) and the reaction stirred at rt. After 45 min, the reaction was briefly warmed to approximately 50° C. and then allowed to cool to rt. After 2.5 hours, an additional 0.0074 mL (0.076 mmol) isopropyl isocyanate was added, the THF evaporated to 1 mL using a stream of nitrogen, the reaction briefly warmed to approximately 50° C. several times, and then stirred at rt overnight. At 21 hours, the reaction was quenched with MeOH, evaporated, then triturated with hot EtOAc to give the title compound as an off-white solid (15.6 mg, 60%). $^{1}$H NMR (DMSO-d6) δ: 10.67 (br. s, 1H), 8.25 (s, 1H), 7.97 (dd, J=8.1, 1.3 Hz, 1H), 7.40-7.46 (m, 1H), 7.34 (d, J=8.8 Hz, 2H), 7.16 (d, J=8.5 Hz, 2H), 6.98-7.09 (m, 2H), 5.96 (d, J=7.3 Hz, 1H), 4.15-4.24 (m, 1H), 3.65-3.80 (m, 2H), 3.44-3.59 (m, 2H), 2.86-2.98 (m, 1H), 1.10 (s, 3H), 1.08 (s, 3H).

Example 15

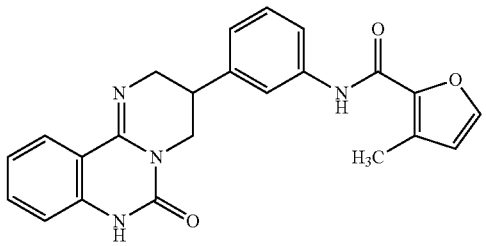 [SMILES: Cc1ccoc1C(=O)Nc1cccc(C2CN=C3c4ccccc4NC(=O)N3C2)c1]

3-Methyl-N-[3-(6-oxo-3,4,6,7-tetrahydro-2H-pyrimido[1,2-c]quinazolin-3-yl)phenyl]-2-furamide A mixture of 3-methyl-furan-2-carboxylic acid (2.4 mg, 0.019 mmol), N,N-diisopropylethylamine (0.017 mL, 0.095 mmol), and BOP (10.1 mg, 0.023 mmol) in 0.6 mL DMF was stirred at rt for 1 hour, then 3-(3-aminophenyl)-2,3,4,7-tetrahydro-6H-pyrimido[1,2-c]quinazolin-6-one (5.0 mg, 0.017 mmol) added and the reaction continued at rt. After 2.5 hours, a small spatula tip of 3-methyl-furan-2-carboxylic acid and BOP was added and the reaction heated at 60° C. for 1 hour. The reaction mixture was partitioned between EtOAc and aqueous Na$_2$CO$_3$ solution, the EtOAc layer washed with H$_2$O, brine, dried with anhydrous Na$_2$SO$_4$ and rotary evaporated. The residue was rinsed with 2 portions of 30% EtOAc/hexane and then chromatographed eluting with 10% MeOH/CHCl$_3$. The resulting solid was chromatographed using a prep plate and eluting with 50% acetone/hexane. The obtained solid was then partitioned between EtOAc and aqueous Na$_2$CO$_3$ solution, the EtOAc layer washed with H$_2$O, brine, dried with anhydrous Na$_2$SO$_4$ and evaporated to give the title compound as a white solid (3.2 mg, 47%). $^1$H NMR (CD$_3$OD/CDCl$_3$ mixture) δ: 8.04 (dd, J=8.2, 1.2 Hz, 1H), 7.68 (t, J=1.8 Hz, 1H), 7.60 (ddd, J=8.1, 2.1, 0.9 Hz, 1H), 7.46-7.53 (m, 2H), 7.37 (t, J=7.9 Hz, 1H), 7.16 (ddd, J=8.1, 7.2, 1.2 Hz, 1H), 7.03-7.10 (m, 2H), 6.45 (dd, J=1.8, 0.6 Hz, 1H), 4.48-4.56 (m, 1H), 3.86-3.95 (m, 1H), 3.61-3.74 (m, 2H), 3.07-3.19 (m, 1H), 2.42 (s, 3H).

Example 16

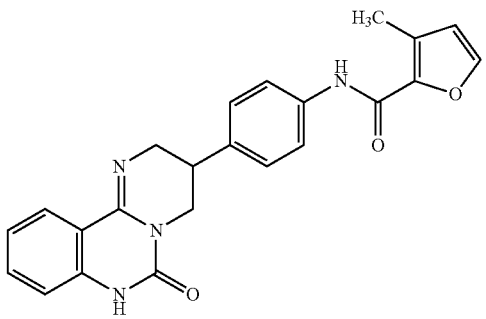 [SMILES: Cc1ccoc1C(=O)Nc1ccc(C2CN=C3c4ccccc4NC(=O)N3C2)cc1]

3-Methyl-N-[4-(6-oxo-3,4,6,7-tetrahydro-2H-pyrimido[1,2-c]quinazolin-3-yl)phenyl]-2-furamide A mixture of 3-methyl-furan-2-carboxylic acid (3.7 mg, 0.029 mmol), N,N-diisopropylethylamine (0.025 mL, 0.145 mmol), and HBTU (13.2 mg, 0.035 mmol) in 0.8 mL DMF was stirred at rt for 10 minutes, then 3-(4-aminophenyl)-2,3,4,7-tetrahydro-6H-pyrimido[1,2-c]quinazolin-6-one (7.6 mg, 0.026 mmol) added and the reaction continued at rt. After 40 min, a spatula tip of 3-methyl-furan-2-carboxylic acid and HBTU was added, the reaction briefly warmed to approximately 60° C. several times, then allowed to cool to rt. At 1.25 hours the reaction mixture was partitioned between EtOAc and aqueous Na$_2$CO$_3$ solution, the EtOAc layer washed with H$_2$O, brine, dried with anhydrous Na$_2$SO$_4$ and rotary evaporated. The resulting solid was chromatographed on a prep plate eluting with 15% MeOH/CHCl$_3$. The obtained solid was then partitioned between EtOAc and aqueous Na$_2$CO$_3$ solution, the EtOAc layer washed with H$_2$O, brine, dried with anhydrous Na$_2$SO$_4$ and rotary evaporated to give the title compound as an off-white solid (7.6 mg, 86%). $^1$H NMR (CD$_3$OD/CDCl$_3$ mixture) δ: 8.03 (dd, J=7.9, 1.2 Hz, 1H), 7.65-7.71 (m, 2H), 7.43-7.52 (m, 2H), 7.26-7.32 (m, 2H), 7.14 (ddd, J=8.1, 7.2, 1.2 Hz, 1H), 7.00-7.05 (m, 1H), 6.45 (d, J=1.5 Hz, 1H), 4.45 (ddd, J=13.0, 4.4, 2.8 Hz, 1H), 3.83-3.91 (m, 1H), 3.59-3.70 (m, 2H), 3.04-3.16 (m, 1H), 2.42 (s, 3H)

Example 17

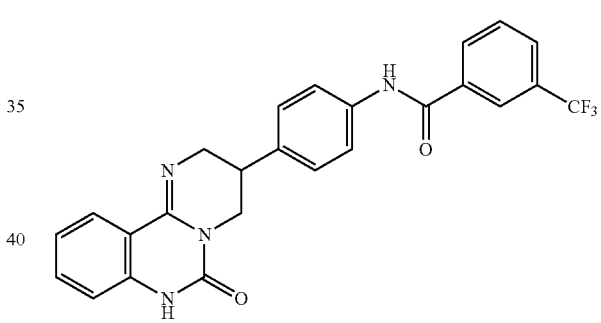

N-[4-(6-oxo-3,4,6,7-tetrahydro-2H-pyrimido[1,2-c]quinazolin-3-yl)phenyl]-3-(trifluoromethyl)benzamide To a solution of 3-(4-aminophenyl)-2,3,4,7-tetrahydro-6H-pyrimido[1,2-c]quinazolin-6-one (10.8 mg, 0.037 mmol) in 0.7 mL pyridine at rt was added 3-(trifluoromethyl)benzoyl chloride (0.0066 mL, 0.044 mmol) and the reaction stirred at rt. After 5 min, the reaction was briefly warmed to dissolve solids and then allowed to cool to rt. At 45 min an additional amount (pipet tip) of 3-(trifluoromethyl)benzoyl chloride was added, the reaction briefly warmed, and then allowed to stir at rt overnight. At 24 hours the reaction was quenched with MeOH and evaporated. The crude mixture was partitioned between EtOAc and aqueous Na$_2$CO$_3$ solution, the EtOAc layer washed with brine, dried with Na$_2$SO$_4$, and evaporated. The resulting solid was triturated with hot EtOAc, hexane added, the solid filtered and rinsed with 30% EtOAc/hexane to give the title compound as an off-white solid (10.3 mg, 60%). $^1$H NMR (CD$_3$OD/CDCl$_3$ mixture) δ: 8.25 (s, 1H), 8.18 (d, J=7.6 Hz, 1H), 8.02 (dd, J=8.1, 1.3 Hz, 1H), 7.84 (d, J=7.9 Hz, 1H), 7.65-7.75 (m, 3H), 7.43-7.50 (m, 1H), 7.29-

7.35 (m, 2H), 7.10-7.17 (m, 1H), 7.00-7.05 (m, 1H), 4.39-4.47 (m, 1H), 3.81-3.90 (m, 1H), 3.61-3.72 (m, 2H), 3.07-3.18 (m, 1H).

Preparation 8

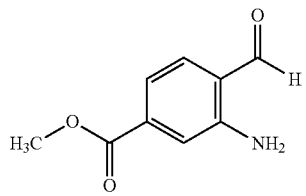

Methy 3-amino-4-formylbenzoate

Methy 3-amino-4-formylbenzoate was prepared by the method described in J. Amer. Chem. Soc. 2008, 130, 416-417. The title compound was obtained as a yellow solid (197 mg, 46%). $^1$H NMR (CDCl$_3$) δ: 9.96 (s, 1H), 7.55-7.59 (m, 1H), 7.33-7.38 (m, 2H), 6.19 (br. s, 2H), 3.92 (s, 3H).

Preparation 9

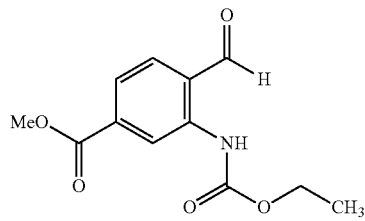 [SMILES: CCOC(=O)Nc1cc(C(=O)OC)ccc1C=O]

Methyl 3-[(ethoxycarbonyl)amino]-4-formylbenzoate

To a mixture of methyl 3-amino-4-formylbenzoate (110 mg, 0.614 mmol) in 6 mL THF plus 4 mL saturated NaHCO$_3$ and 1 mL H$_2$O at rt was added ethyl chloroformate (0.070 mL, 0.737 mmol) at the reaction stirred at rt. After 50 min, an additional 0.5 mL saturated NaHCO$_3$ and 5 drops ethyl chloroformate was added. At 17.5 hours the mixture was heated to 60° C., 1 mL saturated Na$_2$CO$_3$ added, and 5 drops ethyl chloroformate added. Then to push reaction to completion, a small scoop of solid Na$_2$CO$_3$ was added and additional ethyl chloroformate added drop-wise until the reaction was approximately 80% complete (45 hours total reaction time). The reaction was partitioned between EtOAc and aqueous NaHCO$_3$ solution, the EtOAc layer washed with brine, dried with Na$_2$SO$_4$, and evaporated. The solid was crystallized from hexane/EtOAc and the filtrate chromatographed eluting with 2.5% MeOH/CHCl$_3$. The impure products from crystallization and chromatography were combined and then recrystallized from hexane/EtOAc to give the title compound as a light yellow solid (63.8 mg, 41%). $^1$H NMR (CDCl$_3$) δ: 10.53 (br. s, 1H), 10.00 (d, J=0.6 Hz, 1H), 9.11-9.12 (m, 1H), 7.80-7.84 (m, 1H), 7.72-7.76 (m, 1H), 4.28 (q, J=7.2 Hz, 2H), 3.95 (s, 3H), 1.35 (t, J=7.2 Hz, 3H).

Preparation 10

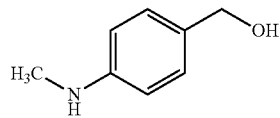

[4-(Methylamino)phenyl]methanol

[4-(Methylamino)phenyl]methanol was prepared by the procedure described in Org. Lett. 2007, 9. 671-674. The title compound was obtained as an off-white solid (1.92 g, 84%). $^1$H NMR (CDCl$_3$) δ: 7.17-7.22 (m, 2H), 6.57-6.63 (m, 2H), 4.55 (s, 2H), 2.84 (s, 3H).

Preparation 11

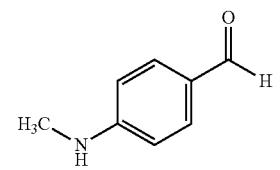

4-(Methylamino)benzaldehyde 4-(Methylamino)benzaldehyde was prepared by the procedure described in J. Amer. Chem. Soc. 2006, 128, 9308-9309. The title compound was obtained as an orange-yellow solid (1.464 g, 77%). $^1$H NMR (CDCl$_3$) δ: 9.73 (s, 1H), 7.68-7.73 (m, 2H), 6.58-6.64 (m, 2H), 4.45 (br. s, 1H), 2.92 (d, J=5.0 Hz, 3H).

Preparation 12

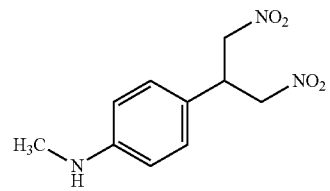 [SMILES: CNc1ccc(C(C[N+](=O)[O-])C[N+](=O)[O-])cc1]

Methyl-4-[2-nitro-1-(nitromethyl)ethyl]aniline

A mixture of 4-(methylamino)benzaldehyde (41 mg, 0.303 mmol) and 50 mg basic aluminum oxide in 1 mL nitromethane was heated at 95° C. After 4 hours the mixture was filtered, rinsed with CHCl$_3$, and evaporated. The crude mixture was chromatographed eluting with gradient 30% to 50% EtOAc/hexane to give the title compound (plus 17 mol % 4-(methylamino)benzaldehyde impurity) as an orange-red oil (43.2 mg, 60%). ¹H NMR (CDCl₃) δ: 6.98-7.04 (m, 2H), 6.54-6.59 (m, 2H), 4.65-4.77 (m, 4H), 4.19 (quin, J=7.3 Hz, 1H), 2.82 (s, 3H).

Preparation 13

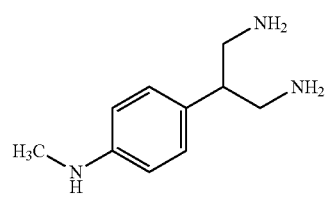

2-[4-(Methylamino)phenyl]propane-1,3-diamine

A mixture of N-methyl-4-[2-nitro-1-(nitromethyl)ethyl] aniline (42.7 mg, 0.178 mmol, 83 mol % purity) and 25 mg platinum (IV) oxide in 4 mL MeOH contained in a pressure tube was reacted under 65 PSI hydrogen. After 20 hours the mixture was filtered past Celite and rinsed with MeOH. The MeOH solution of crude product was stored under N₂ in the freezer and used as is for the next reaction (contained 16 mol % [4-(methylamino)phenyl]methanol impurity). ¹H NMR (CD₃OD) δ: 7.00-7.05 (m, 2H), 6.62-6.68 (m, 2H), 2.83-2.91 (m, 2H), 2.70-2.79 (m, 5H), 2.57-2.67 (m, 1H)

Example 18

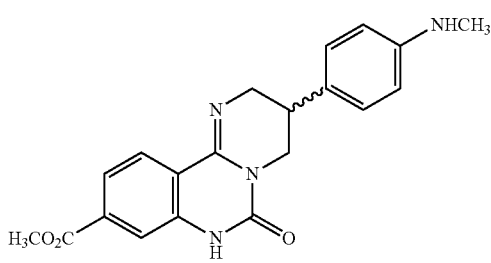 [SMILES: CNc1ccc(C2CN=C3c4ccc(C(=O)OC)cc4NC(=O)N3C2)cc1]

Methyl 3-[4-(methylamino)phenyl]-6-oxo-3,4,6,7-tetrahydro-2H-pyrimido[1,2-c]quinazoline-9-carboxylate The stored MeOH solution of 2-[4-(methylamino)phenyl] propane-1,3-diamine was evaporated just prior to use, then chased with 1 mL t-BuOH to give a clear film (12 mg, 0.067 mmol). To this was added methyl 3-[(ethoxycarbonyl) amino]-4-formylbenzoate (16.8 mg, 0.067 mmol) and powdered K₂CO₃ (46.3 mg, 0.335 mmol) plus 1 mL t-BuOH and the mixture heated at 75° C. At 2 hours iodine (17.0 mg, 0.067 mmol) was added and the reaction heated at 80° C. for 2.25 hours. The reaction was partitioned between EtOAc and aqueous Na₂CO₃ solution plus Na₂S₂O₃, the EtOAc layer washed with brine, dried with Na₂SO₄, and evaporated. The resulting solid was chromatographed eluting with CHCl₃/ MeOH, and then triturated with hot EtOAc to give the title compound as an off-white solid (10.1 mg, 49%). ¹H NMR (CD₃OD) δ: 8.09-8.12 (m, 1H), 7.73 (dd, J=8.4, 1.6 Hz, 1H), 7.66-7.68 (m, 1H), 7.06-7.11 (m, 2H), 6.64-6.70 (m, 2H), 4.41 (ddd, J=13.2, 4.4, 2.9 Hz, 1H), 3.95 (s, 3H), 3.81-3.90 (m, 1H), 3.49-3.65 (m, 2H), 2.91-3.03 (m, 1H), 2.80 (s, 3H)

Example 19

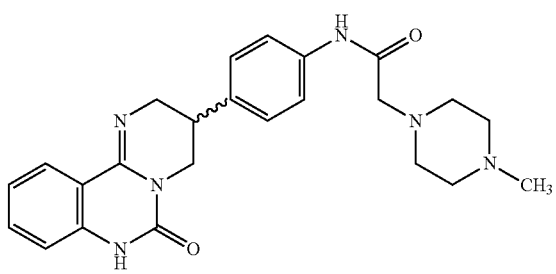 [SMILES: CN1CCN(CC(=O)Nc2ccc(C3CN=C4c5ccccc5NC(=O)N4C3)cc2)CC1]

Methyl 3-(4-{methyl[(4-methylpiperazin-1-yl) acetyl]amino}phenyl)-6-oxo-3,4,6,7-tetrahydro-2H-pyrimido[1,2-c]quinazoline-9-carboxylate A mixture of 3-methyl-furan-2-carboxylic acid (1.9 mg, 0.012 mmol), N,N-diisopropylethylamine (0.0064 mL, 0.037 mmol), and BOP (5.7 mg, 0.013 mmol) in 0.35 mL DMF was stirred at rt for 20 minutes, then methyl 3-[4-(methylamino) phenyl]-6-oxo-3,4,6,7-tetrahydro-2H-pyrimido[1,2-c] quinazoline-9-carboxylate (3.7 mg, 0.010 mmol) added and the reaction continued at rt. After 19 hours, the reaction was heated at 60° C. for 23 hours, then added a small spatula tip of 3-methyl-furan-2-carboxylic acid and BOP plus 0.015 mL N,N-diisopropylethylamine and continued heating at 80° C. for an additional 4 hours. The reaction mixture was partitioned between EtOAc and aqueous Na₂CO₃ solution, the EtOAc layer washed with H₂O, brine, dried with anhydrous Na₂SO₄ and evaporated. The resulting yellow oil was chromatographed on a prep plate eluting with 20% MeOH/CHCl₃ plus NH₄OH. The obtained oily solid was then triturated with EtOAc/hexane to give the title compound as an off-white solid (1.6 mg, 31%). ¹H NMR (CD₃OD/CDCl₃ mixture) δ: 8.14 (d, J=8.2 Hz, 1H), 7.76 (dd, J=8.2, 1.5 Hz, 1H), 7.69 (d, J=0.9 Hz, 1H), 7.41 (d, J=7.9 Hz, 2H), 7.28 (d, J=8.5 Hz, 2H), 4.49 (dt, J=12.6, 3.7 Hz, 1H), 3.96 (s, 4H), 3.66-3.76 (m, 2H), 3.28 (s, 3H), 3.17-3.24 (m, 1H), 3.05 (br. s, 2H), 2.92 (br. s, 4H), 2.62 (br. s, 7H).

Example 20

2-(4-Methylpiperazin-1-yl)-N-[4-(6-oxo-3,4,6,7-tetrahydro-2H-pyrimido[1,2-c]quinazolin-3-yl)phenyl]acetamide A mixture of (4-Methyl-piperazin-1-yl)-acetic acid (3.2 mg, 0.020 mmol), N,N-diisopropylethylamine (0.017 mL, 0.10 mmol), and HBTU (9.1 mg, 0.024 mmol) in 0.6 mL DMF was stirred at rt for 10 minutes, then 3-(4-aminophenyl)-2,3,4,7-tetrahydro-6H-pyrimido[1,2-c]quinazolin-6-one (7.6 mg, 0.026 mmol) added and the reaction continued at rt. At 1.75 hours the reaction mixture was partitioned between EtOAc and aqueous $Na_2CO_3$ solution, the EtOAc layer washed with $H_2O$, brine, dried with anhydrous $Na_2SO_4$ and rotary evaporated to an oily solid. The residue was chromatographed eluting with 10% $MeOH/CHCl_3$ containing $Et_3N$. The obtained oily solid was then partitioned between EtOAc and aqueous $Na_2CO_3$ solution, the EtOAc layer washed with $H_2O$, brine, dried with anhydrous $Na_2SO_4$ and evaporated to give the title compound as a white solid (4.8 mg, 73%). $^1$H NMR ($CDCl_3$) δ: 9.14 (s, 1H), 8.99 (br. s, 1H), 8.11 (d, J=7.9 Hz, 1H), 7.58 (d, J=8.2 Hz, 2H), 7.38-7.44 (m, 1H), 7.22-7.27 (m, 2H), 7.12 (t, J=7.6 Hz, 1H), 6.91 (d, J=8.2 Hz, 1H), 4.53 (dt, J=13.1, 3.6 Hz, 1H), 3.95 (dt, J=16.2, 3.6 Hz, 1H), 3.53-3.69 (m, 2H), 3.15 (s, 2H), 3.00-3.12 (m, 1H), 2.67 (br. s, 4H), 2.52 (br. s, 4H), 2.33 (s, 3H).

Example 21

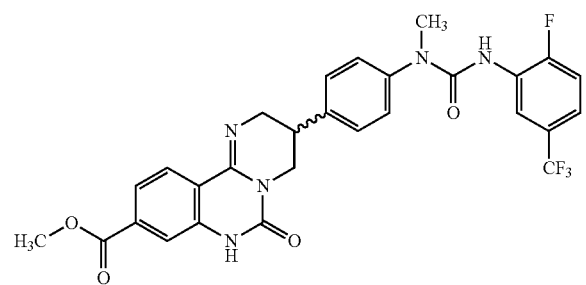 [SMILES: COC(=O)c1ccc2c(c1)NC(=O)N1CC(c3ccc(N(C)C(=O)Nc4cc(C(F)(F)F)ccc4F)cc3)CN=C21]

Methyl 3-{4-[({[2-fluoro-5-(trifluoromethyl)phenyl]amino}carbonyl)(methyl)amino]phenyl}-6-oxo-3,4,6,7-tetrahydro-2H-pyrimido[1,2-c]quinazoline-9-carboxylate To a solution of methyl 3-[4-(methylamino)phenyl]-6-oxo-3,4,6,7-tetrahydro-2H-pyrimido[1,2-c]quinazoline-9-carboxylate (5.1 mg, 0.014 mmol) in 0.7 mL THF was added 2-fluoro-5-(trifluoromethyl)phenyl isocyanate (0.0024 mL, 0.017 mmol) and the reaction stirred at rt. After 15 min, the reaction was briefly warmed to approximately 50° C. and then allowed to cool to rt. At 1 hour the reaction was quenched with 1 mL MeOH and evaporated. The resulting solid was crystallized from EtOAc/hexane to give the title compound as an off-white solid (6.4 mg, 80%). $^1$H NMR (Acetone-d6) δ: 9.70 (br. s, 1H), 8.57 (dd, J=7.3, 2.3 Hz, 1H), 8.21 (d, J=8.2 Hz, 1H), 7.76 (d, J=1.2 Hz, 1H), 7.69 (dd, J=8.4, 1.6 Hz, 1H), 7.50-7.59 (m, 4H), 7.25-7.39 (m, 2H), 7.06 (d, J=2.9 Hz, 1H), 4.39-4.47 (m, 1H), 3.88-3.97 (m, 4H), 3.62-3.79 (m, 2H), 3.34 (s, 3H), 3.15-3.27 (m, 1H).

Preparation 14

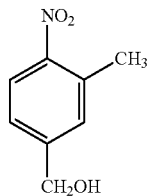

(3-Methyl-4-nitro-phenyl)-methanol

A flask purged with nitrogen was charged with 3-methyl-4-nitro-benzoic acid (72.5 g, 0.400 mol), trimethyl borate (166.2 g, 1.600 mol) and dry tetrahydrofuran (1449 mL). A solution of borane dimethyl sulfide complex (63.8 g, 79.8 mL, 0.840 mol) was added drop-wise to the stirred batch at 20-35° C. over at least 30 min. An exotherm and effervescence were observed during the addition. The mixture was stirred at 65° C. for at least 6 h or until in-process HPLC analysis showed that conversion was greater than 97%. Reaction was quenched at 20-40° C. with cooling by drop-wise addition of methanol (46 mL) followed by aq 5 N hydrochloric acid (144 mL) over at least 30 min. Exotherm and effervescence were observed during the quench. After stirring the batch at 50° C. for at least 1 h, it was concentrated under reduced pressure to a volume of 360 mL. The concentrated batch was washed with water (453 mL) and the solids were collected on a filter. The wet filter cake was dissolved in $CH_2Cl_2$ (2170 mL) at and the resulting solution dried over anhydrous magnesium sulfate (36 g). The dried filtrate solution containing the title compound (~67 g, 100% yield) was used directly in the preparation of 3-methyl-4-nitro-benzaldehyde.

Preparation 15

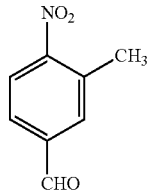

3-Methyl-4-nitro-benzaldehyde

A flask was charged with (3-methyl-4-nitro-phenyl)-methanol (66.9 g, 0.400 mol), manganese(IV) oxide (85%, 5 μm powder, 409.1 g, 4.00 mol), and $CH_2Cl_2$ (1337 mL). The mixture was stirred at 40° C. for at least 2 h or until HPLC analysis showed that the reaction had proceeded to greater the 97% completion. The cooled batch was diluted with $CH_2Cl_2$ (1 L) and filtered through a Celite® pad (34 g), and the filter cake was rinsed with more $CH_2Cl_2$ (1 L). The filtrate and washes were concentrated under in vacuo to dryness to give the title compound as a yellow solid (58 g, 87% yield).

Preparation 16

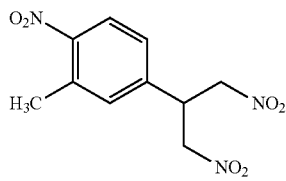

2-Methyl-1-nitro-4-(2-nitro-1-nitromethyl-ethyl)-benzene

Crude 3-methyl-4-nitro-benzaldehyde (57.8 g, 0.35 mol), basic aluminum oxide (71.4 g, 0.700 mol), and nitromethane (427.3 g, 379 mL, 7.00 mol) were charged to a flask. The mixture was stirred at 100° C. for >3 h or until HPLC analysis showed that the reaction had proceeded to greater the 97% completion. The cooled reaction mixture was filtered through a celite pad (29 g) and the filter cake rinsed with $CH_2Cl_2$ (1.2 L). The filtrate and wash were concentrated under reduced pressure to dryness at 50° C. The residue was dissolved in acetone (1.2 L) and treated with charcoal (29 g) with stirring at 50° C. for at least 1 h. The slurry was filtered through a celite pad (29 g) and the filter cake was rinsed with acetone (1.2 L). The filtrate and wash were concentrated to dryness in vacuo. The concentrated product (~48 g, ~51% mass recovery) was dissolved in ethyl acetate (120 mL) at 75° C. and hexane (400 mL) was added drop-wise at 60-75° C. to induce crystallization. The resulting suspension was filtered at 20-25° C. to give the title compound as a yellow solid (36 g, 38% yield).

Preparation 17

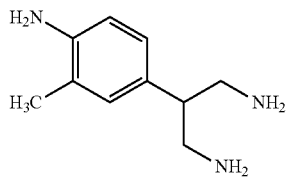

2-(4-Amino-3-methyl-phenyl)-propane-1,3-diamine

A heavy-walled flask under $N_2$ was charged with 10 wt % platinum on carbon (3.8 g), 10 wt % palladium on carbon (50% wet, 11.3 g), Raney Ni (wet, 11.3 g), 2-methyl-1-nitro-4-(2-nitro-1-nitromethyl-ethyl)-benzene (37.7 g, 0.14 mol), and MeOH (754 mL). After attaching the flask to the hydrogenation apparatus, it was subjected to three vacuum degas-nitrogen purge cycles, followed by three nitrogen outgas-hydrogen purge cycles. The resulting suspension was stirred under 60 psi of $H_2$ at 55-60° C. for at least 72 h. The reaction mixture was filtered through a celite pad (27 g), rinsing with methanol (760 mL). The filtrate and rinse were concentrated to dryness in vacuo to give the crude title compound as red-brown gum (24 g, 96% yield). This material was used without further purification.

Preparation 18

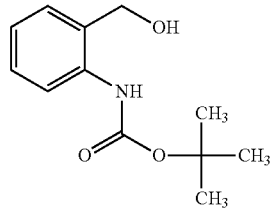 [SMILES: CC(C)(C)OC(=O)Nc1ccccc1CO]

(2-Hydroxymethyl-phenyl)-carbamic acid tert-butyl ester

A flask was charged with crude (2-Amino-phenyl)-methanol (24.6 g, 0.200 mol), $CH_2Cl_2$ (172 mL), and N,N-diisopropylethylamine (33.6 g, 0.260 mol) and purged with nitrogen. Stirring was initiated and the solution was treated dropwise with a solution of di-t-butyl dicarbonate (54.6 g, 0.250 mol) in $CH_2Cl_2$ (75 mL) at 15-20° C. over about 30 min. The reaction mixture was stirred at 20-30° C. for at least 18 h or until HPLC analysis showed that the reaction had proceeded to greater the 97% completion. The reaction mixture was washed sequentially with water (100 mL), 10 wt % aqueous orthophosphoric acid (2×75 mL) and water (75 mL). The separated organic layer was dried over anhydrous magnesium sulfate (12 g), filtered, and concentrated to dryness under reduced pressure to afford the title compound as an oily brown material (48 g, quantitative).

Preparation 19

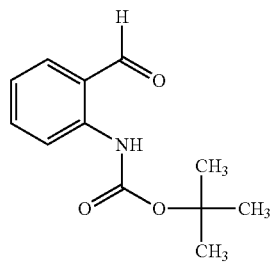 [SMILES: CC(C)(C)OC(=O)Nc1ccccc1C=O]

(2-Formyl-phenyl)-carbamic acid tert-butyl ester (2-Hydroxymethyl-phenyl)-carbamic acid tert-butyl ester (44.7 g, 0.200 mol), $CH_2Cl_2$ (625 mL) and manganese(IV) oxide (85%, 5 μm powder; 245.5 g, 2.400 mol) were introduced into a flask. The mixture was stirred at 40° C. for at least 4 h or until HPLC analysis showed that the reaction had proceeded to greater than 97% completion. The cooled mixture was filtered through a Celite pad (22 g) and the filter cake was rinsed with $CH_2Cl_2$ (625 mL). The filtrate and wash were concentrated in vacuo to dryness to afford the title compound as an oily yellow material (44 g, 99% yield).

Example 22

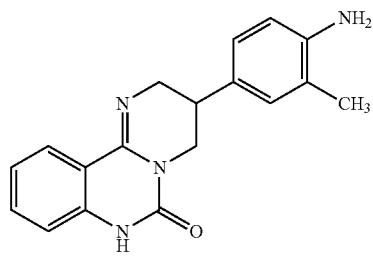 [SMILES: Cc1cc(C2CN=C3c4ccccc4NC(=O)N3C2)ccc1N]

3-(4-amino-3-methylphenyl)-2,3,4,7-tetrahydro-6H-pyrimido[1,2-c]quinazolin-6-one A flask was charged with (2-formyl-phenyl)-carbamic acid tert-butyl ester (8.8 g, 0.040 mol), 2-(4-amino-3-methyl-phenyl)-propane-1,3-diamine (10.0 g, 0.056 mol), t-butanol (177 mL), and N,N-dimethylformamide (53 mL). The mixture was stirred at 70-80° C. for 3 h. To the stirred, cooled (40-50° C.) mixture were added anhydrous potassium carbonate (16.6 g) and iodine (20.3 g). The batch was then stirred at 80° C. for at least 5 h or until HPLC analysis showed that the reaction had proceeded to greater the 98% completion. The cooled reaction mixture was filtered through a celite pad (8.8 g) and the filter cake was rinsed with MeOH (110 mL). The filtrate and rinse were diluted with toluene (90 mL) and concentrated to dryness under reduced pressure. The residue was stirred with aqueous 20 wt % sodium thiosulfate pentahydrate (180 mL) for 1 h at ambient temperature. This mixture was extracted with $CH_2Cl_2$ (2×180 mL) and the separated organic layers were concentrated to dryness in vacuo. The concentrate (20 g) was dissolved with methanol (10 mL) and loaded onto a Biotage KP-Sil SNAP cartridge (100 g) that had been pre-equilibrated with 300 mL 5% v/v triethylamine in hexane. A Biotage unit was used to elute the cartridge with an ethyl acetate-hexane gradient (0% to 80%). Clean fractions were collected, combined, and concentrated to dryness under reduced pressure as quickly as possible to provide the title compound as a yellow solid (2.9 g 23% yield).

Preparation 20

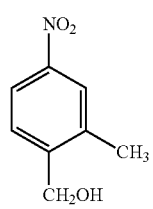

(2-Methyl-4-nitro-phenyl)-methanol

A flask was purged with nitrogen and charged with 2-methyl-4-nitro-benzoic acid (45.3 g, 0.25 mol), trimethyl borate (103.9 g, 1.00 mol), and tetrahydrofuran (906 mL). Neat borane dimethyl sulfide complex (39.9 g, 49.8 mL, 0.525 mol) was added drop-wise at 20-35° C. over at least 30 min. An exotherm and effervescence were observed during this addition. When the addition was complete, the reaction mixture was stirred at 65° C. for at least 2 h or until in-process HPLC analysis showed that conversion was greater than 97%. The batch was quenched with cooling by drop-wise addition of methanol (46 mL), followed by a solution of 12.1 N aqueous hydrochloric acid (97 g, 82.1 mL, 1.00 mol) in water (138 mL) over at least 30 min. Batch temperature was held at 20-35° C. during quench; an exotherm and effervescence were observed during the quench. The mixture was stirred at 50° C. for at least 1 h and concentrated under reduced pressure to a volume of ~230 mL (to remove tetrahydrofuran). The concentrate was diluted with water (453 mL) and extracted with ethyl acetate (2×453 mL). The organic layer was washed with saturated aqueous sodium chloride solution (230 mL), dried over anhydrous magnesium sulfate (23 g), filtered, and concentrated in vacuo to dryness to give the title compound as a beige solid (41 g, 98% yield).

Preparation 21

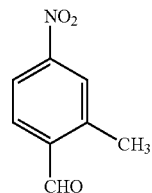

2-Methyl-4-nitro-benzaldehyde

A flask was charged with (2-methyl-4-nitro-phenyl)-methanol (16.7 g, 0.100 mol) (334 mL), to manganese(IV) oxide (5 μm, 102.3 g, 1.00 mol), and $CH_2Cl_2$ (334 mL). The stirred mixture was heated at 40° C. for at least 2 h or until in-process HPLC analysis showed that conversion was greater than 95%. The cooled mixture was filtered through a celite cake (8 g) loaded onto a fritted funnel and the filter cake was rinsed with $CH_2Cl_2$ (340 mL). The filtrate and wash were concentrated under reduced pressure to dryness to afford the title compound as an amorphous solid (13.0 g, 78% yield).

Preparation 22

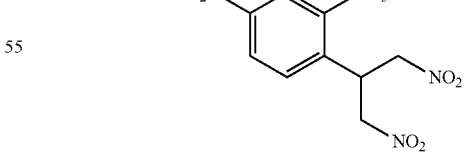

2-Methyl-4-nitro-1-(2-nitro-1-nitromethyl-ethyl)-benzene

A flask was charged with crude 2-methyl-4-nitro-benzaldehyde (21.5 g, 0.13 mol), aluminum oxide (27 g, 0.26 mol), and nitromethane (159 g, 141 mL, 2.6 mol). The mixture was stirred under nitrogen at 100° C. for at least 3 h until in-process HPLC analysis showed that conversion was greater than 97%. After cooling, the mixture was filtered through Celite® (11 g) and the filter cake was rinsed with CH$_2$Cl$_2$ (430 mL). The filtrate was concentrated to dryness at 50° C. in vacuo; the residue was dissolved in acetone (430 mL) and treated with charcoal (11 g) at 50° C. for at least 1 h. Filtration through Celite® (11 g), rinsing with acetone (210 mL) provided a filtrate which was concentrated to dryness under reduced pressure. This material was dissolved in ethyl acetate (60 mL) at 75° C., to which hexane (240 mL) was added drop-wise with stirring at 60-75° C. to induce crystallization. The resulting suspension was cooled and filtered to give the title compound as a yellow solid (22 g, 63% yield).

Preparation 23

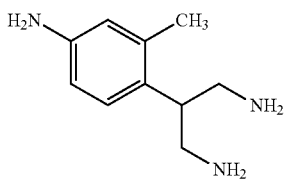 [SMILES: Cc1cc([N+](=O)[O-])ccc1C(C[N+](=O)[O-])C[N+](=O)[O-]]

2-(4-Amino-2-methyl-phenyl)-propane-1,3-diamine

A pressure flask was charged with 2-methyl-4-nitro-1-(2-nitro-1-nitromethyl-ethyl)-benzene (29.6 g, 0.11 mol), 10 wt % platinum on carbon (3.0 g), 10 wt % palladium on carbon (9.0 g, 50 wt % water), Raney nickel (9.0 g, wet), and methanol (740 mL) under a nitrogen blanket. After attaching the flask to the hydrogenation apparatus, it was subjected to three vacuum degas-nitrogen purge cycles, followed by three nitrogen outgas-hydrogen purge cycles. The vigorously stirred suspension was held under 60 psi hydrogen pressure at 55-60° C. for at least 72 h. The reaction mixture was filtered through a celite pad (15 g) rinsing with methanol (600 mL). The filtrate was concentrated to dryness under reduced pressure to give the crude title compound as a red-brown gum (20 g, 100% yield).

Example 23

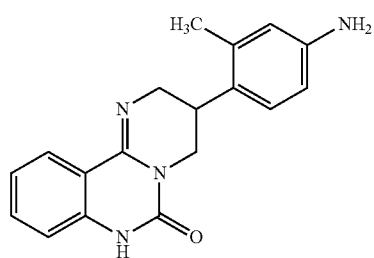 [SMILES: Cc1cc(N)ccc1C1CN=C2c3ccccc3NC(=O)N2C1]

3-(4-amino-2-methylphenyl)-2,3,4,7-tetrahydro-6H-pyrimido[1,2-c]quinazolin-6-one A flask was charged with (2-Formyl-phenyl)-carbamic acid tert-butyl ester (8.8 g, 0.040 mol), 2-(4-Amino-2-methyl-phenyl)-propane-1,3-diamine (10.0 g, 0.056 mol), t-butanol (177 mL), and N,N-dimethylformamide (53 mL) and purged well with nitrogen. The mixture was stirred at 75° C. for at least 3 h. To the cooled mixture were added anhydrous potassium carbonate (16.6 g) and iodine (12.2 g). The batch was stirred at 80° C. for 10 h. The cooled mixture was filtered through a celite pad (4.4 g) and the filter cake was rinsed with methanol (177 mL). The filtrate and wash were diluted with toluene (88 mL) and concentrated to dryness under reduced pressure. The residue was stirred with aqueous 15 wt % sodium thiosulfate pentahydrate (88 mL) and saturated aqueous sodium chloride (44 mL) for 1 h at ambient temperature. The resulting mixture was extracted with CH$_2$Cl$_2$ (2×177 mL). The separated organic layer was dried over anhydrous magnesium sulfate (4.4 g), filtered, and concentrate to dryness in vacuo. The concentrate (20 g) was dissolved with methanol (20 mL) and loaded onto a KP-Sil samplet (34 g). The sample was allowed to dry before loading it into a Biotage KP-Sil SNAP cartridge (340 g). A Biotage unit was used to elute the cartridge with a ethyl acetate-hexane gradient (0% to 90%). Clean fractions were collected, combined, and concentrated to dryness under reduced pressure to provide the title compound as a yellow solid (1.6 g, 13% yield).

Example 24

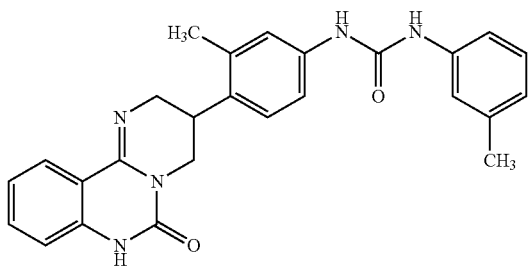 [SMILES: Cc1cccc(NC(=O)Nc2ccc(C3CN=C4c5ccccc5NC(=O)N4C3)c(C)c2)c1]

1-[3-methyl-4-(6-oxo-3,4,6,7-tetrahydro-2H-pyrimido[1,2-c]quinazolin-3-yl)phenyl]-3-(3-methylphenyl)urea To a mixture of 3-(4-amino-2-methylphenyl)-2,3,4,7-tetrahydro-6H-pyrimido[1,2-c]quinazolin-6-one (92 mg, 0.30 mmol) and triethylamine (0.125 mL, 0.90 mmol) in 2.5 mL CH$_2$Cl$_2$ at rt was added meta-tolyl isocyanate (0.057 mL, 0.45 mmol) and the reaction stirred at rt. After 2 hours, an additional 0.015 mL meta-tolyl isocyanate and 1.5 mL CH$_2$Cl$_2$ was added and the reaction continued for 20 hours. The reaction was quenched with 0.5 mL MeOH, stirred 5 minutes and then evaporated. The mixture was triturated with MeOH, filtered and rinsed with MeOH and EtOAc to give the title compound as an off-white solid (99 mg, 75%). $^1$H NMR (DMSO-d6) δ: 10.68 (s, 1H), 8.54 (d, J=3.2 Hz, 2H), 7.99 (dd, J=7.9, 1.5 Hz, 1H), 7.40-7.47 (m, 1H), 7.00-7.32 (m, 8H), 6.78 (d, J=7.0 Hz, 1H), 4.15-4.23 (m, 1H), 3.63-3.73 (m, 1H), 3.44-3.55 (m, 2H), 3.04-3.16 (m, 1H), 2.31 (s, 3H), 2.27 (s, 3H).

Example 25

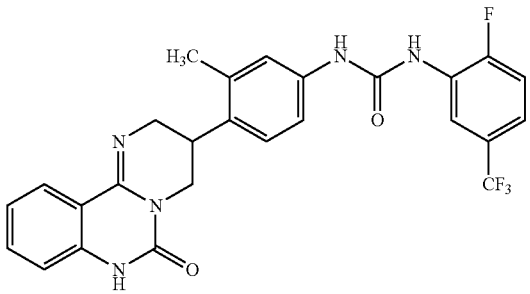 [SMILES: Cc1cc(NC(=O)Nc2cc(C(F)(F)F)ccc2F)ccc1C1CN=C2c3ccccc3NC(=O)N2C1]

1-[2-fluoro-5-(trifluoromethyl)phenyl]-3-[3-methyl-4-(6-oxo-3,4,6,7-tetrahydro-2H-pyrimido[1,2-c]quinazolin-3-yl)phenyl]urea To a mixture of 3-(4-amino-2-methylphenyl)-2,3,4,7-tetrahydro-6H-pyrimido[1,2-c]quinazolin-6-one (92 mg, 0.30 mmol) and triethylamine (0.125 mL, 0.90 mmol) in 2.5 mL $CH_2Cl_2$ at rt was added 2-fluoro-5-(trifluoromethyl)phenyl isocyanate (0.065 mL, 0.45 mmol) and the reaction stirred at rt. After 2.5 hours the reaction was quenched with 0.3 mL MeOH, and then stored overnight in the refrigerator. The reaction mixture was filtered and rinsed with EtOAc to give the title compound as an off-white solid (130 mg, 84%). $^1$H NMR (DMSO-d6) δ: 10.69 (s, 1H), 9.09 (s, 1H), 8.87 (d, J=2.9 Hz, 1H), 8.63 (dd, J=7.5, 2.2 Hz, 1H), 7.99 (dd, J=7.9, 1.2 Hz, 1H), 7.33-7.53 (m, 4H), 7.24-7.29 (m, 1H), 7.13-7.17 (m, 1H), 7.00-7.10 (m, 2H), 4.15-4.23 (m, 1H), 3.64-3.73 (m, 1H), 3.46-3.56 (m, 2H), 3.07-3.15 (m, 1H), 2.33 (s, 3H)

The present invention is not to be limited in scope by the exemplified embodiments which are intended as illustrations of single aspects of the invention only. Indeed, various modifications of the invention in addition to those described herein will become apparent to those skilled in the art from the foregoing description. For example, the novel compounds of this invention include any compound which is a 4-aryl-substituted-(2H)-pyrimido[1,2-c]quinazoline-6-oxo, e.g. a substituted 4-phenyl-substituted-(2H)-pyrimido[1,2-c]quinazoline-6-oxo, wherein said 4-aryl, e.g. said 4-phenyl is substituted with a carboamino, or an aminocarbo or an aminocarboamino aryl group and binds to a tyrosine kinase receptor, e.g. a VEGF and/or PDGF receptor.

Preferably, said 4-aryl, e.g. said 4-phenyl, is linked to said carboamino, aminocarbo or aminocarboamino aryl by a linking group represented by the formula —$(NR^5)_p$—C(O)—$(NR^6)_q$— wherein p is 0 or 1 and q is 0 or 1 and $R^5$ and $R^6$ are as defined above.

These compounds may be prepared and tested for tyrosine kinase inhibiting activity by the preparatory methods and assays disclosed above.

Such modifications are intended to fall within the scope of the appended claims.

All references cited herein are hereby incorporated by reference in their entirety. Also, the compounds of the present invention may be tested by the various in-vitro and in-vivo assays disclosed in such references to demonstrate the claimed utilities.

We claim:
1. A compound represented by Formula I:

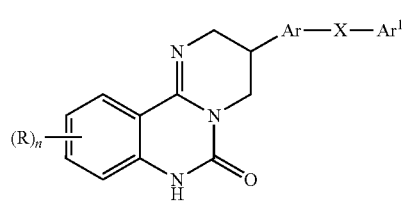

or a pharmaceutically acceptable salt, thereof, wherein:
Ar is an phenyl group;
$Ar^1$ is an phenyl or furanyl group;
X is

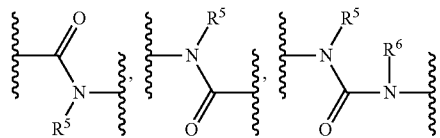

R is selected from the group consisting of lower alkyl, $OC(O)R^4$, $(CR^1R^2)_aC(O)OR^3$, $(CR^1R^2)_aOR^3$, $(CR^1R^2)_aN(R^4)C(O)R^3$, $(CR^1R^2)_aC(O)N(R^3)_2$, $(CR^1R^2)_aN(R^4)C(O)OR^3$, $(CR^1R^2)_aN(R^4)C(O)N(R^3)_2$, $(CR^1R^2)_aN(R^3)_2$, wherein $N(R^3)_2$ may form a heterocyclic ring optionally substituted with one or more of halogen and lower alkyl;
$R^1$, $R^2$ and $R^4$ are independently selected from the group consisting of hydrogen, halogen and lower alkyl;
$R^3$ is selected from the group consisting of hydrogen and lower alkyl;
$R^5$ is selected from hydrogen and lower alkyl;
$R^6$ is selected from hydrogen and lower alkyl;
a is 0 or an integer of from 1 to 4; and
n is 0 or an integer of from 1 to 4.

2. The compound of a claim 1 wherein $Ar^1$ is a phenyl or furanyl group substituted with one or more substituents selected from a halo, lower alkyl, lower alkyloxy, lower alkylthio or halo-lower alkyl group.

3. The compound of a claim 1 wherein $Ar^1$ is a phenyl or furanyl group substituted with one or more substituents selected from a methyl, methoxy, methylthio, bromo, fluoro, trifluoro, or chloro group.

4. The compound of claim 3 wherein $Ar^1$ is selected from the group consisting of a fluoro and trifluoro-substituted phenyl.

5. The compound of claim 1 wherein R is selected from the group consisting of hydrogen and acetate.

6. The compound of claim 1 wherein a is 0.

7. The compound of claim 1 wherein n is 0 or 1.

8. The compound of claim 7 wherein n is 0.

9. The compound of claim 1 selected from the group consisting of:
1-[2-fluoro-5-(trifluoromethyl)phenyl]-3-[3-(6-oxo-3,4,6,7-tetrahydro-2H-pyrimido[1,2-c]quinazolin-3-yl)phenyl]urea,
1-[2-fluoro-5-(trifluoromethyl)phenyl]-3-[4-(6-oxo-3,4,6,7-tetrahydro-2H-pyrimido[1,2-c]quinazolin-3-yl)phenyl]urea,
1-[4-(6-oxo-3,4,6,7-tetrahydro-2H-pyrimido[1,2-c]quinazolin-3-yl)phenyl]-3-phenylurea, 1-[4-chloro-3-

(trifluoromethyl)phenyl]-3-[4-(6-oxo-3,4,6,7-tetrahydro-2H-pyrimido[1,2-c]quinazolin-3-yl)phenyl]urea,
1-[3-(methylthio)phenyl]-3-[4-(6-oxo-3,4,6,7-tetrahydro-2H-pyrimido[1,2-c]quinazolin-3-yl)phenyl]urea,
1-(3-bromophenyl)-3-[4-(6-oxo-3,4,6,7-tetrahydro-2H-pyrimido[1,2-c]quinazolin-3-yl)phenyl]urea,
1-(3-methylphenyl)-3-[4-(6-oxo-3,4,6,7-tetrahydro-2H-pyrimido[1,2-c]quinazolin-3-yl)phenyl]urea,
1-(4-methylphenyl)-3-[4-(6-oxo-3,4,6,7-tetrahydro-2H-pyrimido[1,2-c]quinazolin-3-yl)phenyl]urea,
1-(4-methoxyphenyl)-3-[4-(6-oxo-3,4,6,7-tetrahydro-2H-pyrimido[1,2-c]quinazolin-3-yl)phenyl]urea,
1-(3-methoxyphenyl)-3-[4-(6-oxo-3,4,6,7-tetrahydro-2H-pyrimido[1,2-c]quinazolin-3-yl)phenyl]urea,
3-methyl-N-[3-(6-oxo-3,4,6,7-tetrahydro-2H-pyrimido[1,2-c]quinazolin-3-yl)phenyl]-2-furamide,
3-methyl-N-[4-(6-oxo-3,4,6,7-tetrahydro-2H-pyrimido[1,2-c]quinazolin-3-yl)phenyl]-2-furamide,
N-[4-(6-oxo-3,4,6,7-tetrahydro-2H-pyrimido[1,2-c]quinazolin-3-yl)phenyl]-3-(trifluoromethyl)benzamide, and
methyl 3-{4-[({[2-fluoro-5-(trifluoromethyl)phenyl]amino}carbonyl)(methyl)amino]phenyl}-6-oxo-3,4,6,7-tetrahydro-2H-pyrimido[1,2-c]quinazoline-9-carboxylate;
1-[3-methyl-4-(6-oxo-3,4,6,7-tetrahydro-2H-pyrimido[1,2-c]quinazolin-3-yl)phenyl]-3-(3-methylphenyl)urea; and
1-[2-fluoro-5-(trifluoromethyl)phenyl]-3-[3-methyl-4-(6-oxo-3,4,6,7-tetrahydro-2H-pyrimido[1,2-c]quinazolin-3-yl)phenyl]urea; or a pharmaceutically acceptable salt thereof.

10. The compound of claim 9, selected from group consisting of:
1-[2-fluoro-5-(trifluoromethyl)phenyl]-3-[3-(6-oxo-3,4,6,7-tetrahydro-2H-pyrimido[1,2-c]quinazolin-3-yl)phenyl]urea,
1-[2-fluoro-5-(trifluoromethyl)phenyl]-3-[4-(6-oxo-3,4,6,7-tetrahydro-2H-pyrimido[1,2-c]quinazolin-3-yl)phenyl]urea,
1-[4-chloro-3-(trifluoromethyl)phenyl]-3-[4-(6-oxo-3,4,6,7-tetrahydro-2H-pyrimido[1,2-c]quinazolin-3-yl)phenyl]urea,
1-(3-bromophenyl)-3-[4-(6-oxo-3,4,6,7-tetrahydro-2H-pyrimido[1,2-c]quinazolin-3-yl)phenyl]urea,
1-(3-methylphenyl)-3-[4-(6-oxo-3,4,6,7-tetrahydro-2H-pyrimido[1,2-c]quinazolin-3-yl)phenyl]urea and
3-methyl-N-[3-(6-oxo-3,4,6,7-tetrahydro-2H-pyrimido[1,2-c]quinazolin-3-yl)phenyl]-2-furamide; and
1-[2-fluoro-5-(trifluoromethyl)phenyl]-3-[3-methyl-4-(6-oxo-3,4,6,7-tetrahydro-2H-pyrimido[1,2-c]quinazolin-3-yl)phenyl]urea; or a pharmaceutically acceptable salt thereof.

11. A pharmaceutical composition comprising at least one compound of claim 1, or a pharmaceutically acceptable salt thereof, and at least one pharmaceutically acceptable carrier or excipient.

* * * * *

UNITED STATES PATENT AND TRADEMARK OFFICE
CERTIFICATE OF CORRECTION

PATENT NO.       : 9,365,575 B2
APPLICATION NO.  : 13/897837
DATED            : June 14, 2016
INVENTOR(S)      : Thomas C. Malone et al.

Page 1 of 1

It is certified that error appears in the above-identified patent and that said Letters Patent is hereby corrected as shown below:

On the title page, item (56), in column 2, under "Other Publications", line 3, delete "Invenst.," and insert -- Invest., --, therefor.

In the specification,

In column 3, line 51, delete "aryl;" and insert -- aryl. --, therefor.

In column 33, lines 9-15 (Structure), delete " 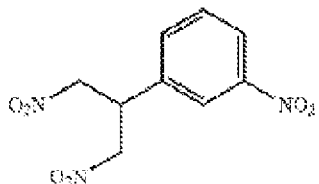 " and insert -- 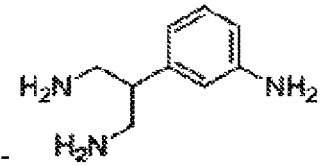 --, therefor.

In column 35, line 24, delete "Pan" and insert -- Parr --, therefor.

In column 42, line 46, delete "oxo" and insert -- Oxo --, therefor.

In column 43, line 20, delete "Methy" and insert -- Methyl --, therefor.

In column 43, line 22, delete "Methy" and insert -- Methyl --, therefor.

In column 52, line 39, before "manganese(IV)" delete "to".

In the claims,

In column 56, line 42, in Claim 2, delete "of a" and insert -- of --, therefor.

In column 56, line 46, in Claim 3, delete "of a" and insert -- of --, therefor.

Signed and Sealed this
Twenty-third Day of August, 2016

Michelle K. Lee
*Director of the United States Patent and Trademark Office*